(12) United States Patent
Yip et al.

(10) Patent No.: US 8,014,952 B2
(45) Date of Patent: Sep. 6, 2011

(54) SERUM BIOMARKERS IN LUNG CANCER

(75) Inventors: Timothy Tak Chun Yip, Hong Kong (CN); Chi Shing Cho, Hong Kong (CN); Siu Kie Au, Kowloon (CN); Tai-Tung Yip, Cupertino, CA (US); Christine Yip, Cupertino, CA (US); Victor Yip, Union City, CA (US)

(73) Assignees: Queen Elizabeth Hospital, Hong Kong (HK); Vermillion, Inc., Fremont, CA (US)

( * ) Notice: Subject to any disclaimer, the term of this patent is extended or adjusted under 35 U.S.C. 154(b) by 884 days.

(21) Appl. No.: 10/539,291

(22) PCT Filed: Dec. 16, 2003

(86) PCT No.: PCT/US03/37090
§ 371 (c)(1),
(2), (4) Date: Apr. 7, 2006

(87) PCT Pub. No.: WO2004/061410
PCT Pub. Date: Jul. 22, 2004

(65) Prior Publication Data
US 2006/0223127 A1 Oct. 5, 2006

Related U.S. Application Data

(60) Provisional application No. 60/434,075, filed on Dec. 18, 2002.

(51) Int. Cl.
*G01N 33/48* (2006.01)
(52) U.S. Cl. ....................................... 702/19
(58) Field of Classification Search ................ 702/19
See application file for complete search history.

(56) References Cited

U.S. PATENT DOCUMENTS
2003/0091976 A1  5/2003  Boschetti et al.

OTHER PUBLICATIONS

Tatyana A. Zhukov et al., "Discovery of distinct protien profiling specific for lung tumors and pre-malignant lung lesions by SELDI mass spectrometry", Proceedings of the American Association for Cancer Research Annual Meeting, vol. 43, Mar. 2002, pp. 36 XP001207903 & 93RD Annual Meeting of the American Association for Cancer Research, San Francisco, CA; USA; Apr. 6-10, 2002.
Terry W. Moody et al., "Surface enhanced laser desorption/ionization analysis of human lung cancer specimens", Proceedings of the American Association for Cancer Research Annual Meeting, vol, 42, Mar. 2001, pp. 59, XP001207590 & 92ND Annual Meeting of the American Association for Cancer Research; New Orleans, LA USA Mar. 24-28, 2001.
Weiguo Wu et al., "Rapid screening and identification of serum tumor-associated markers in patients with respectable non-small cell lung cancer:", Proceedings of the American Association for Cancer Research Annual Meeting, vol. 43, Mar. 2002, pp. 756, XP001207589 & 93RD Annual Meeting of the American Association for Cancer Research; San Francisco, CA, Apr. 6-10, 2002.
M D Benson et al., "Serum Amyloid A in Carcinoma of the Lung", Cancer, vol. 57, No. 9, 1986, pp. 1783-1787.
International Search Report of PCT/US03/37090.
K. Chapman, "The Protein Chip Biomarker System from Ciphergen Biosystems: a novel proteomics platform for rapid biomarker discovery and validation", Biochemical Society Transactions. Apr. 2002, vol. 30, part 2, pp. 82-87.
Poon et al., "Comprehensive Proteomic Profiling Identifies Serum Proteomic Signatures for Detection of Hepatocellular Carcinoma and Its Subtypes", Clinical Chemistry, May 2003, vol. 49, No. 5, pp. 752-760.

*Primary Examiner* — Jerry Lin
(74) *Attorney, Agent, or Firm* — Stephen A. Bent; Foley & Lardner LLP

(57) ABSTRACT

Certain biomarkers and biomarker combinations are useful in a qualifying lung cancer status in a subject. A diagnostic methodology employing these biomarkers and combinations can detect whether a subject has lung cancer.

| MARKER ID | MW | FRACTION |
|---|---|---|
| IM-1 | 2011 | A |
| IM-2 | 2030 | A |
| IM-3 | 2069 | A |
| IM-4 | 2128 | A |
| IM-5 | 2146 | A |
| IM-6 | 2186 | A |
| IM-7 | 2232 | A |
| IM-8 | 2277 | A |
| IM-9 | 2295 | A |
| IM-10 | 2318 | A |
| IM-11 | 2411 | A |
| IM-12 | 2434 | A |
| IM-13 | 2467 | A |
| IM-14 | 2482 | A |
| IM-15 | 2498 | A |
| IM-16 | 2565 | A |
| IM-17 | 2574 | A |
| IM-18 | 2586 | A |
| IM-19 | 2605 | A |
| IM-20 | 2722 | A |
| IM-21 | 2746 | A |
| IM-22 | 2788 | A |
| IM-23 | 2855 | A |
| IM-24 | 2871 | A |
| IM-25 | 2984 | A |
| IM-26 | 3030 | A |
| IM-27 | 3144 | A |
| IM-28 | 3243 | A |
| IM-29 | 3273 | A |
| IM-30 | 3290 | A |
| IM-31 | 3369 | A |
| IM-32 | 3445 | A |
| IM-33 | 3483 | A |
| IM-34 | 3676 | A |
| IM-35 | 3779 | A |
| IM-36 | 3793 | A |
| IM-37 | 3893 | A |
| IM-38 | 3960 | A |
| IM-39 | 3972 | A |
| IM-40 | 3984 | A |
| IM-41 | 4068 | A |
| IM-42 | 4178 | A |
| IM-43 | 4287 | A |
| IM-44 | 4297 | A |
| IM-45 | 4309 | A |

| MARKER ID | MW | FRACTION | MARKER ID | MW | FRACTION |
|---|---|---|---|---|---|
| IM-46 | 4484 | A | IM-97 | 2451 | B |
| IM-47 | 4649 | A | IM-98 | 2468 | B |
| IM-48 | 4798 | A | IM-99 | 2483 | B |
| IM-49 | 5104 | A | IM-100 | 2565 | B |
| IM-50 | 5918 | A | IM-101 | 2583 | B |
| IM-51 | 6122 | A | IM-102 | 2597 | B |
| IM-52 | 6192 | A | IM-103 | 2697 | B |
| IM-53 | 6452 | A | IM-104 | 2715 | B |
| IM-54 | 6660 | A | IM-105 | 2740 | B |
| IM-55 | 7768 | A | IM-106 | 2752 | B |
| IM-56 | 8145 | A | IM-107 | 2767 | B |
| IM-57 | 8954 | A | IM-108 | 2885 | B |
| IM-58 | 9312 | A | IM-109 | 2882 | B |
| IM-59 | 9449 | A | IM-110 | 2967 | B |
| IM-60 | 10272 | A | IM-111 | 2977 | B |
| IM-61 | 11683 | A | IM-112 | 2994 | B |
| IM-62 | 13376 | A | IM-113 | 3031 | B |
| IM-63 | 14698 | A | IM-114 | 3048 | B |
| IM-64 | 15190 | A | IM-115 | 3148 | B |
| IM-64 | 66758 | A | IM-116 | 3166 | B |
| IM-65 | 15951 | A | IM-117 | 3283 | B |
| IM-66 | 15172 | A | IM-118 | 3308 | B |
| IM-67 | 15925 | A | IM-119 | 3332 | B |
| IM-68 | 23436 | A | IM-120 | 3432 | B |
| IM-69 | 39794 | A | IM-121 | 3450 | B |
| IM-70 | 44166 | A | IM-122 | 3561 | B |
| IM-71 | 48890 | A | IM-123 | 3615 | B |
| IM-72 | 54028 | A | IM-124 | 3714 | B |
| IM-73 | 60170 | A | IM-125 | 3730 | B |
| IM-75 | 74372 | A | IM-126 | 3834 | B |
| IM-76 | 75545 | A | IM-127 | 3899 | B |
| IM-77 | 77543 | A | IM-128 | 3969 | B |
| IM-78 | 79507 | A | IM-129 | 3986 | B |
| IM-79 | 88854 | A | IM-130 | 3997 | B |
| IM-80 | 101831 | A | IM-131 | 4013 | B |
| IM-81 | 104301 | A | IM-132 | 4181 | B |
| IM-82 | 125160 | A | IM-133 | 4297 | B |
| IM-83 | 132978 | A | IM-134 | 4311 | B |
| IM-84 | 149099 | A | IM-135 | 4465 | B |
| IM-85 | 2016 | B | IM-136 | 4484 | B |
| IM-86 | 2029 | B | IM-137 | 4579 | B |
| IM-87 | 2144 | B | IM-138 | 4608 | B |
| IM-88 | 2130 | B | IM-139 | 4669 | B |
| IM-89 | 2168 | B | IM-140 | 4747 | B |
| IM-90 | 2164 | B | IM-141 | 4862 | B |
| IM-91 | 2200 | B | IM-142 | 4891 | B |
| IM-92 | 2284 | B | IM-143 | 5033 | B |
| IM-93 | 2299 | B | IM-144 | 5077 | B |
| IM-94 | 2314 | B | | | |
| IM-95 | 2414 | B | | | |
| IM-96 | 2428 | B | | | |

3 Claims, 46 Drawing Sheets

FIGURE 1A

| MARKER ID | MW | FRACTION | MARKER ID | MW | FRACTION | MARKER ID | MW | FRACTION |
|---|---|---|---|---|---|---|---|---|
| IM-1 | 2011 | A | IM-37 | 3893 | A | IM-72 | 54026 | A |
| IM-2 | 2030 | A | IM-38 | 3960 | A | IM-73 | 60170 | A |
| IM-3 | 2069 | A | IM-39 | 3972 | A | IM-75 | 74372 | A |
| IM-4 | 2128 | A | IM-40 | 3984 | A | IM-76 | 75545 | A |
| IM-5 | 2146 | A | IM-41 | 4066 | A | IM-77 | 77543 | A |
| IM-6 | 2186 | A | IM-42 | 4178 | A | IM-78 | 79507 | A |
| IM-7 | 2232 | A | IM-43 | 4287 | A | IM-79 | 89854 | A |
| IM-8 | 2277 | A | IM-44 | 4297 | A | IM-80 | 101831 | A |
| IM-9 | 2295 | A | IM-45 | 4309 | A | IM-81 | 104301 | A |
| IM-10 | 2318 | A | IM-46 | 4484 | A | IM-82 | 125160 | A |
| IM-11 | 2411 | A | IM-47 | 4649 | A | IM-83 | 132976 | A |
| IM-12 | 2434 | A | IM-48 | 4798 | A | IM-84 | 149099 | A |
| IM-13 | 2467 | A | IM-49 | 5104 | A | IM-85 | 2016 | B |
| IM-14 | 2482 | A | IM-50 | 5918 | A | IM-86 | 2029 | B |
| IM-15 | 2498 | A | IM-51 | 6122 | A | IM-87 | 2144 | B |
| IM-16 | 2565 | A | IM-52 | 6192 | A | IM-88 | 2130 | B |
| IM-17 | 2574 | A | IM-53 | 6452 | A | IM-89 | 2168 | B |
| IM-18 | 2586 | A | IM-54 | 6660 | A | IM-90 | 2184 | B |
| IM-19 | 2605 | A | IM-55 | 7766 | A | IM-91 | 2200 | B |
| IM-20 | 2722 | A | IM-56 | 8145 | A | IM-92 | 2284 | B |
| IM-21 | 2746 | A | IM-57 | 8954 | A | IM-93 | 2299 | B |
| IM-22 | 2788 | A | IM-58 | 9312 | A | IM-94 | 2314 | B |
| IM-23 | 2855 | A | IM-59 | 9449 | A | IM-95 | 2414 | B |
| IM-24 | 2871 | A | IM-60 | 10272 | A | IM-96 | 2428 | B |
| IM-25 | 2984 | A | IM-61 | 11663 | A | IM-97 | 2451 | B |
| IM-26 | 3030 | A | IM-62 | 13376 | A | IM-98 | 2466 | B |
| IM-27 | 3144 | A | IM-63 | 14698 | A | IM-99 | 2483 | B |
| IM-28 | 3243 | A | IM-64 | 15190 | A | IM-100 | 2565 | B |
| IM-29 | 3273 | A | IM-64 | 66758 | A | IM-101 | 2583 | B |
| IM-30 | 3290 | A | IM-65 | 15951 | A | IM-102 | 2597 | B |
| IM-31 | 3369 | A | IM-66 | 15172 | A | IM-103 | 2697 | B |
| IM-32 | 3445 | A | IM-67 | 15925 | A | IM-104 | 2715 | B |
| IM-33 | 3483 | A | IM-68 | 23436 | A | IM-105 | 2740 | B |
| IM-34 | 3676 | A | IM-69 | 39794 | A | IM-106 | 2752 | B |
| IM-35 | 3779 | A | IM-70 | 44166 | A | IM-107 | 2767 | B |
| IM-36 | 3793 | A | IM-71 | 46890 | A | IM-108 | 2865 | B |
| | | | | | | IM-109 | 2882 | B |
| | | | | | | IM-110 | 2967 | B |
| | | | | | | IM-111 | 2977 | B |
| | | | | | | IM-112 | 2994 | B |
| | | | | | | IM-113 | 3031 | B |
| | | | | | | IM-114 | 3048 | B |
| | | | | | | IM-115 | 3148 | B |
| | | | | | | IM-116 | 3166 | B |
| | | | | | | IM-117 | 3283 | B |
| | | | | | | IM-118 | 3308 | B |
| | | | | | | IM-119 | 3332 | B |
| | | | | | | IM-120 | 3432 | B |
| | | | | | | IM-121 | 3450 | B |
| | | | | | | IM-122 | 3561 | B |
| | | | | | | IM-123 | 3615 | B |
| | | | | | | IM-124 | 3714 | B |
| | | | | | | IM-125 | 3730 | B |
| | | | | | | IM-126 | 3834 | B |
| | | | | | | IM-127 | 3899 | B |
| | | | | | | IM-128 | 3969 | B |
| | | | | | | IM-129 | 3986 | B |
| | | | | | | IM-130 | 3997 | B |
| | | | | | | IM-131 | 4013 | B |
| | | | | | | IM-132 | 4181 | B |
| | | | | | | IM-133 | 4297 | B |
| | | | | | | IM-134 | 4311 | B |
| | | | | | | IM-135 | 4465 | B |
| | | | | | | IM-136 | 4484 | B |
| | | | | | | IM-137 | 4579 | B |
| | | | | | | IM-138 | 4608 | B |
| | | | | | | IM-139 | 4669 | B |
| | | | | | | IM-140 | 4747 | B |
| | | | | | | IM-141 | 4862 | B |
| | | | | | | IM-142 | 4891 | B |
| | | | | | | IM-143 | 5033 | B |
| | | | | | | IM-144 | 5077 | B |

FIGURE 1B

| MARKER ID | MW | FRACTION | MARKER ID | MW | FRACTION | MARKER ID | MW | FRACTION |
|---|---|---|---|---|---|---|---|---|
| IM-145 | 5099 | B | IM-181 | 16018 | B | IM-217 | 2130 | C | IM-253 | 3733 | C |
| IM-146 | 5143 | B | IM-182 | 17346 | B | IM-218 | 2145 | C | IM-254 | 3833 | C |
| IM-147 | 5158 | B | IM-183 | 18311 | B | IM-219 | 2167 | C | IM-255 | 3900 | C |
| IM-148 | 5272 | B | IM-184 | 22586 | B | IM-220 | 2182 | C | IM-256 | 4010 | C |
| IM-149 | 5306 | B | IM-185 | 23422 | B | IM-221 | 2199 | C | IM-257 | 4145 | C |
| IM-150 | 5349 | B | IM-186 | 27969 | B | IM-222 | 2211 | C | IM-258 | 4187 | C |
| IM-151 | 5364 | B | IM-187 | 33283 | B | IM-223 | 2230 | C | IM-259 | 4299 | C |
| IM-152 | 5421 | B | IM-188 | 39808 | B | IM-224 | 2250 | C | IM-260 | 4466 | C |
| IM-153 | 5554 | B | IM-189 | 43110 | B | IM-225 | 2280 | C | IM-261 | 4582 | C |
| IM-154 | 5711 | B | IM-190 | 44454 | B | IM-226 | 2297 | C | IM-262 | 4813 | C |
| IM-155 | 5876 | B | IM-191 | 47215 | B | IM-227 | 2317 | C | IM-263 | 4876 | C |
| IM-156 | 5916 | B | IM-192 | 53784 | B | IM-228 | 2412 | C | IM-264 | 5032 | C |
| IM-157 | 5931 | B | IM-193 | 55952 | B | IM-229 | 2428 | C | IM-265 | 5347 | C |
| IM-158 | 5988 | B | IM-194 | 60573 | B | IM-230 | 2468 | C | IM-266 | 5365 | C |
| IM-159 | 6137 | B | IM-195 | 66346 | B | IM-231 | 2481 | C | IM-267 | 5932 | C |
| IM-160 | 6200 | B | IM-196 | 73387 | B | IM-232 | 2498 | C | IM-268 | 7767 | C |
| IM-161 | 6443 | B | IM-197 | 79203 | B | IM-233 | 2567 | C | IM-269 | 7973 | o |
| IM-162 | 6644 | B | IM-198 | 89302 | B | IM-234 | 2585 | C | IM-270 | 8143 | C |
| IM-163 | 6958 | B | IM-199 | 94226 | B | IM-235 | 2599 | C | IM-271 | 9187 | C |
| IM-164 | 7481 | B | IM-200 | 99358 | B | IM-236 | 2698 | C | IM-272 | 9293 | C |
| IM-165 | 7568 | B | IM-201 | 102096 | B | IM-237 | 2715 | C | IM-273 | 11705 | C |
| IM-166 | 7765 | B | IM-202 | 107199 | B | IM-238 | 2745 | C | IM-274 | 14041 | C |
| IM-167 | 7955 | B | IM-203 | 116936 | B | IM-239 | 2766 | C | IM-275 | 15114 | C |
| IM-168 | 8144 | B | IM-204 | 119487 | B | IM-240 | 2867 | C | IM-276 | 15939 | C |
| IM-169 | 8698 | B | IM-205 | 122103 | B | IM-241 | 2885 | C | IM-277 | 22321 | C |
| IM-170 | 8821 | B | IM-206 | 125431 | B | IM-242 | 2998 | C | IM-278 | 28001 | C |
| IM-171 | 8944 | B | IM-207 | 132052 | B | IM-243 | 3052 | C | IM-279 | 33296 | C |
| IM-172 | 9138 | B | IM-208 | 138518 | B | IM-244 | 3096 | C | IM-280 | 39770 | C |
| IM-173 | 9298 | B | IM-209 | 145147 | B | IM-245 | 3151 | C | IM-281 | 44460 | C |
| IM-174 | 9390 | B | IM-210 | 157502 | B | IM-246 | 3167 | C | IM-282 | 47307 | C |
| IM-175 | 9516 | B | IM-211 | 168579 | B | IM-247 | 3286 | C | IM-283 | 50625 | C |
| IM-176 | 11711 | B | IM-212 | 173391 | B | IM-248 | 3303 | C | IM-284 | 55898 | C |
| IM-177 | 11914 | B | IM-213 | 2011 | C | IM-249 | 3335 | C | IM-285 | 60882 | C |
| IM-178 | 14033 | B | IM-214 | 2030 | C | IM-250 | 3448 | C | IM-286 | 66294 | C |
| IM-179 | 15110 | B | IM-215 | 2050 | C | IM-251 | 3619 | C | IM-287 | 78892 | C |
| IM-180 | 15838 | B | IM-216 | 2096 | C | IM-252 | 3709 | C | IM-288 | 83848 | C |

FIGURE 1C

| MARKER ID | MW | FRACTION | MARKER ID | MW | FRACTION | MARKER ID | MW | FRACTION | MARKER ID | MW | FRACTION |
|---|---|---|---|---|---|---|---|---|---|---|---|
| IM-289 | 89081 | C | IM-325 | 2565 | D | IM-361 | 13857 | D | IM-397 | 2082 | E |
| IM-290 | 94147 | C | IM-326 | 2582 | D | IM-362 | 14056 | D | IM-398 | 2128 | E |
| IM-291 | 99324 | C | IM-327 | 2597 | D | IM-363 | 15108 | D | IM-399 | 2148 | E |
| IM-292 | 107163 | C | IM-328 | 2716 | D | IM-364 | 15844 | D | IM-400 | 2170 | E |
| IM-293 | 110350 | C | IM-329 | 2747 | D | IM-365 | 22243 | D | IM-401 | 2187 | E |
| IM-294 | 113339 | C | IM-330 | 2767 | D | IM-366 | 25465 | D | IM-402 | 2206 | E |
| IM-295 | 116291 | C | IM-331 | 2866 | D | IM-367 | 28022 | D | IM-403 | 2232 | E |
| IM-296 | 122769 | C | IM-332 | 2882 | D | IM-368 | 33272 | D | IM-404 | 2250 | E |
| IM-297 | 131908 | C | IM-333 | 2994 | D | IM-369 | 40149 | D | IM-405 | 2279 | E |
| IM-298 | 145248 | C | IM-334 | 3032 | D | IM-370 | 43113 | D | IM-406 | 2296 | E |
| IM-299 | 159252 | C | IM-335 | 3050 | D | IM-371 | 44219 | D | IM-407 | 2314 | E |
| IM-300 | 165164 | C | IM-336 | 3148 | D | IM-372 | 47196 | D | IM-408 | 2354 | E |
| IM-301 | 174928 | D | IM-337 | 3164 | D | IM-373 | 51062 | D | IM-409 | 2394 | E |
| IM-302 | 196003 | D | IM-338 | 3278 | D | IM-374 | 56082 | D | IM-410 | 2413 | E |
| IM-303 | 2007 | D | IM-339 | 3334 | D | IM-375 | 58239 | D | IM-411 | 2436 | E |
| IM-304 | 2016 | D | IM-340 | 3385 | D | IM-376 | 60285 | D | IM-412 | 2457 | E |
| IM-305 | 2030 | D | IM-341 | 3432 | D | IM-377 | 66148 | D | IM-413 | 2466 | E |
| IM-306 | 2052 | D | IM-342 | 3451 | D | IM-378 | 73668 | D | IM-414 | 2499 | E |
| IM-307 | 2099 | D | IM-343 | 3617 | D | IM-379 | 77433 | D | IM-415 | 2566 | E |
| IM-308 | 2130 | D | IM-344 | 3701 | D | IM-380 | 79986 | D | IM-416 | 2583 | E |
| IM-309 | 2144 | D | IM-345 | 3725 | D | IM-381 | 80844 | D | IM-417 | 2612 | E |
| IM-310 | 2154 | D | IM-346 | 3833 | D | IM-382 | 89962 | D | IM-418 | 2662 | E |
| IM-311 | 2166 | D | IM-347 | 3899 | D | IM-383 | 94399 | D | IM-419 | 2723 | E |
| IM-312 | 2184 | D | IM-348 | 4008 | D | IM-384 | 99419 | D | IM-420 | 2738 | E |
| IM-313 | 2204 | D | IM-349 | 4157 | D | IM-385 | 108395 | D | IM-421 | 2750 | E |
| IM-314 | 2231 | D | IM-350 | 4297 | D | IM-386 | 116433 | D | IM-422 | 2849 | E |
| IM-315 | 2252 | D | IM-351 | 4580 | D | IM-387 | 123337 | D | IM-423 | 2867 | E |
| IM-316 | 2275 | D | IM-352 | 4805 | D | IM-388 | 131977 | D | IM-424 | 3036 | E |
| IM-317 | 2299 | D | IM-353 | 6946 | D | IM-389 | 145658 | D | IM-425 | 3147 | E |
| IM-318 | 2316 | D | IM-354 | 7053 | D | IM-390 | 152603 | D | IM-426 | 3281 | E |
| IM-319 | 2412 | D | IM-355 | 7767 | D | IM-391 | 158524 | D | IM-427 | 3319 | E |
| IM-320 | 2435 | D | IM-356 | 7954 | D | IM-392 | 196072 | D | IM-428 | 3445 | E |
| IM-321 | 2466 | D | IM-357 | 8139 | D | IM-393 | 2010 | E | IM-429 | 3693 | E |
| IM-322 | 2480 | D | IM-358 | 9292 | D | IM-394 | 2029 | E | IM-430 | 3731 | E |
| IM-323 | 2499 | D | IM-359 | 11671 | D | IM-395 | 2050 | E | IM-431 | 3818 | E |
| IM-324 | 2518 | D | IM-360 | 13727 | D | IM-396 | 2068 | E | IM-432 | 3885 | E |

FIGURE 1D

| MARKER ID | MW | FRACTION | MARKER ID | MW | FRACTION | MARKER ID | MW | FRACTION | MARKER ID | MW | FRACTION |
|---|---|---|---|---|---|---|---|---|---|---|---|
| IM-433 | 4136 | E | IM-469 | 86211 | E | IM-505 | 4174 | F | IM-541 | 95033 | F |
| IM-434 | 4169 | E | IM-470 | 89407 | E | IM-506 | 4362 | F | IM-542 | 100310 | F |
| IM-435 | 4257 | E | IM-471 | 100270 | E | IM-507 | 4473 | F | IM-543 | 116889 | F |
| IM-436 | 4277 | E | IM-472 | 109638 | E | IM-508 | 4631 | F | IM-544 | 132711 | F |
| IM-437 | 4355 | E | IM-473 | 117132 | E | IM-509 | 4822 | F | IM-545 | 147276 | F |
| IM-438 | 4369 | E | IM-474 | 132843 | E | IM-510 | 5862 | F | IM-546 | 160768 | F |
| IM-439 | 4470 | E | IM-475 | 147160 | E | IM-511 | 6192 | F | | | |
| IM-440 | 4486 | E | IM-476 | 152199 | E | IM-512 | 6941 | F | | | |
| IM-441 | 4541 | E | IM-477 | 166461 | E | IM-513 | 7626 | F | | | |
| IM-442 | 4634 | E | IM-478 | 176635 | E | IM-514 | 7772 | F | | | |
| IM-443 | 4841 | E | IM-479 | 2011 | F | IM-515 | 7957 | F | | | |
| IM-444 | 5862 | E | IM-480 | 2030 | F | IM-516 | 8150 | F | | | |
| IM-445 | 5911 | E | IM-481 | 2128 | F | IM-517 | 8954 | F | | | |
| IM-446 | 6649 | E | IM-482 | 2149 | F | IM-518 | 9300 | F | | | |
| IM-447 | 6952 | E | IM-483 | 2186 | F | IM-519 | 11545 | F | | | |
| IM-448 | 7769 | E | IM-484 | 2207 | F | IM-520 | 11717 | F | | | |
| IM-449 | 8148 | E | IM-485 | 2279 | F | IM-521 | 13887 | F | | | |
| IM-450 | 8260 | E | IM-486 | 2299 | F | IM-522 | 14073 | F | | | |
| IM-451 | 8785 | E | IM-487 | 2319 | F | IM-523 | 15196 | F | | | |
| IM-452 | 9301 | E | IM-488 | 2412 | F | IM-524 | 15903 | F | | | |
| IM-453 | 10071 | E | IM-489 | 2434 | F | IM-525 | 22460 | F | | | |
| IM-454 | 11721 | E | IM-490 | 2467 | F | IM-526 | 23135 | F | | | |
| IM-455 | 13910 | E | IM-491 | 2485 | F | IM-527 | 28135 | F | | | |
| IM-456 | 15919 | E | IM-492 | 2582 | F | IM-528 | 33577 | F | | | |
| IM-457 | 22422 | E | IM-493 | 2605 | F | IM-529 | 39813 | F | | | |
| IM-458 | 28233 | E | IM-494 | 2697 | F | IM-530 | 42344 | F | | | |
| IM-459 | 33490 | E | IM-495 | 2751 | F | IM-531 | 43274 | F | | | |
| IM-460 | 43121 | E | IM-496 | 2865 | F | IM-532 | 44345 | F | | | |
| IM-461 | 44558 | E | IM-497 | 3036 | F | IM-533 | 51007 | F | | | |
| IM-462 | 46694 | E | IM-498 | 3151 | F | IM-534 | 56318 | F | | | |
| IM-463 | 50954 | E | IM-499 | 3372 | F | IM-535 | 60079 | F | | | |
| IM-464 | 54478 | E | IM-500 | 3440 | F | IM-536 | 66690 | F | | | |
| IM-465 | 60041 | E | IM-501 | 3488 | F | IM-537 | 75122 | F | | | |
| IM-466 | 66652 | E | IM-502 | 3717 | F | IM-538 | 78429 | F | | | |
| IM-467 | 75580 | E | IM-503 | 3890 | F | IM-539 | 81249 | F | | | |
| IM-468 | 79463 | E | IM-504 | 4155 | F | IM-540 | 89384 | F | | | |

FIGURE 2

| RANK | MW | MARKER ID | RANK | MW | MARKER ID |
|---|---|---|---|---|---|
| 1 | 14073 | IM-522 | 39 | 117132 | IM-473 |
| 2 | 11705 | IM-273 | 40 | 13727 | IM-360 |
| 3 | 11717 | IM-520 | 41 | 4257 | IM-435 |
| 4 | 11545 | IM-519 | 42 | 5349 | IM-150 |
| 5 | 11721 | IM-454 | 43 | 5364 | IM-151 |
| 6 | 4473 | IM-507 | 44 | 2967 | IM-110 |
| 7 | 13887 | IM-521 | 45 | 6122 | IM-51 |
| 8 | 5272 | IM-148 | 46 | 6958 | IM-163 |
| 9 | 5365 | IM-266 | 47 | 4355 | IM-437 |
| 10 | 75122 | IM-537 | 48 | 160768 | IM-546 |
| 11 | 100270 | IM-471 | 49 | 5554 | IM-153 |
| 12 | 5862 | IM-510 | 50 | 7767 | IM-268 |
| 13 | 132711 | IM-544 | | | |
| 14 | 132843 | IM-474 | | | |
| 15 | 5876 | IM-155 | | | |
| 16 | 5932 | IM-157 | | | |
| 17 | 11711 | IM-176 | | | |
| 18 | 5911 | IM-445 | | | |
| 19 | 11914 | IM-177 | | | |
| 20 | 4486 | IM-440 | | | |
| 21 | 79463 | IM-468 | | | |
| 22 | 4369 | IM-438 | | | |
| 23 | 100310 | IM-542 | | | |
| 24 | 11671 | IM-359 | | | |
| 25 | 4277 | IM-436 | | | |
| 26 | 2752 | IM-106 | | | |
| 27 | 13910 | IM-455 | | | |
| 28 | 5862 | IM-444 | | | |
| 29 | 5988 | IM-158 | | | |
| 30 | 5347 | IM-265 | | | |
| 31 | 5918 | IM-50 | | | |
| 32 | 6137 | IM-159 | | | |
| 33 | 5916 | IM-156 | | | |
| 34 | 4470 | IM-439 | | | |
| 35 | 5931 | IM-157 | | | |
| 36 | 4631 | IM-508 | | | |
| 37 | 7772 | IM-514 | | | |
| 38 | 176635 | IM-478 | | | |

Figure 30.
84106
88780
162375
166898
84125
88712
162354
161441
84472
84133
WM-714  F
WM-715  F
WM-718  F
WM-717  F

Figure 4A

| Rank | Normal vs Cancer | Adeno vs Normal | Squamous vs Normal | Small Cell vs Normal | Non-small Cell vs Normal | Large Cell vs Normal | Adeno vs Squamous | Adeno vs Small Cell | Squamous vs Small Cell |
|---|---|---|---|---|---|---|---|---|---|
| 1 | WM-61 | WM-447 | WM-447 | WM-70 | WM-341 | WM-16 | WM-62 | WM-457 | WM-276 |
| 2 | WM-447 | WM-652 | WM-61 | WM-706 | WM-342 | WM-26 | WM-415 | WM-72 | WM-277 |
| 3 | WM-446 | WM-61 | WM-277 | WM-369 | WM-343 | WM-499 | WM-152 | WM-369 | WM-362 |
| 4 | WM-133 | WM-446 | WM-446 | WM-447 | WM-48 | WM-134 | WM-385 | WM-78 | WM-257 |
| 5 | WM-119 | WM-290 | WM-133 | WM-61 | WM-340 | WM-647 | WM-347 | WM-79 | WM-363 |
| 6 | WM-278 | WM-363 | WM-134 | WM-652 | WM-346 | WM-277 | WM-134 | WM-73 | WM-347 |
| 7 | WM-134 | WM-133 | WM-363 | WM-282 | WM-47 | WM-310 | WM-36 | WM-64 | WM-53 |
| 8 | WM-363 | WM-341 | WM-362 | WM-446 | WM-339 | WM-363 | WM-108 | WM-320 | WM-254 |
| 9 | WM-282 | WM-285 | WM-276 | WM-456 | WM-389 | WM-446 | WM-99 | WM-419 | WM-17 |
| 10 | WM-362 | WM-366 | WM-706 | WM-134 | WM-669 | WM-221 | WM-151 | WM-85 | WM-252 |
| 11 | WM-120 | WM-282 | WM-203 | WM-203 | WM-447 | WM-648 | WM-289 | WM-82 | WM-431 |
| 12 | WM-280 | WM-362 | WM-466 | WM-648 | WM-652 | WM-657 | WM-363 | WM-53 | WM-513 |
| 13 | WM-65 | WM-310 | WM-388 | WM-455 | WM-154 | WM-290 | WM-61 | WM-440 | WM-446 |
| 14 | WM-277 | WM-292 | WM-65 | WM-65 | WM-587 | WM-328 | WM-117 | WM-412 | WM-355 |
| 15 | WM-70 | WM-120 | WM-70 | WM-685 | WM-456 | WM-447 | WM-211 | WM-455 | WM-447 |
| 16 | WM-369 | WM-134 | WM-341 | WM-473 | WM-450 | WM-684 | WM-362 | WM-313 | WM-133 |
| 17 | WM-17 | WM-276 | WM-429 | WM-343 | WM-283 | WM-183 | WM-133 | WM-456 | WM-245 |
| 18 | WM-473 | WM-428 | WM-347 | WM-466 | WM-207 | WM-190 | WM-414 | WM-86 | WM-52 |
| 19 | WM-47 | WM-277 | WM-17 | WM-341 | WM-436 | WM-686 | WM-277 | WM-70 | WM-96 |
| 20 | WM-203 | WM-20 | WM-47 | WM-340 | WM-384 | WM-397 | WM-141 | WM-246 | WM-238 |
| 21 | WM-276 | WM-119 | WM-431 | WM-353 | WM-61 | WM-466 | WM-64 | WM-360 | WM-243 |
| 22 | WM-279 | WM-340 | WM-62 | WM-339 | WM-167 | WM-20 | WM-135 | WM-190 | WM-138 |
| 23 | WM-62 | WM-48 | WM-473 | WM-457 | WM-382 | WM-17 | WM-447 | WM-418 | WM-62 |
| 24 | WM-366 | WM-389 | WM-384 | WM-86 | WM-285 | WM-545 | WM-383 | WM-83 | WM-580 |
| 25 | WM-456 | WM-450 | WM-438 | WM-506 | WM-650 | WM-47 | WM-338 | WM-257 | WM-134 |
| 26 | WM-428 | WM-47 | WM-652 | WM-72 | WM-203 | WM-191 | WM-63 | WM-138 | WM-240 |
| 27 | WM-384 | WM-343 | WM-282 | WM-287 | WM-119 | WM-147 | WM-142 | WM-47 | WM-256 |
| 28 | WM-287 | WM-17 | WM-389 | WM-82 | WM-282 | WM-480 | WM-446 | WM-252 | WM-203 |
| 29 | WM-420 | WM-583 | WM-290 | WM-528 | WM-686 | WM-590 | WM-186 | WM-282 | WM-111 |
| 30 | WM-292 | WM-70 | WM-278 | WM-85 | WM-383 | WM-218 | WM-111 | WM-60 | WM-95 |
| 31 | WM-431 | WM-706 | WM-456 | WM-73 | WM-429 | WM-285 | WM-445 | WM-68 | WM-247 |
| 32 | WM-455 | WM-346 | WM-873 | WM-138 | WM-11 | WM-652 | WM-455 | WM-325 | WM-157 |
| 33 | WM-20 | WM-466 | WM-340 | WM-384 | WM-208 | WM-651 | WM-276 | WM-402 | WM-242 |
| 34 | WM-340 | WM-646 | WM-55 | WM-83 | WM-451 | WM-388 | WM-444 | WM-411 | WM-556 |
| 35 | WM-19 | WM-384 | WM-455 | WM-450 | WM-473 | WM-403 | WM-181 | WM-75 | WM-63 |
| 36 | WM-389 | WM-336 | WM-645 | WM-310 | WM-220 | WM-418 | WM-35 | WM-405 | WM-239 |
| 37 | WM-63 | WM-294 | WM-138 | WM-277 | WM-685 | WM-430 | WM-285 | WM-417 | WM-234 |
| 38 | WM-438 | WM-339 | WM-420 | WM-79 | WM-338 | WM-456 | WM-456 | WM-387 | WM-274 |

Figure 4B

| | | | | | | | |
|---|---|---|---|---|---|---|---|
| 39 | WM-450 | WM-473 | WM-450 | WM-207 | WM-71 | WM-714 | WM-39 | WM-26 | WM-370 |
| 40 | WM-466 | WM-369 | WM-369 | WM-278 | WM-268 | WM-646 | WM-82 | WM-410 | WM-301 |
| 41 | WM-296 | WM-38 | WM-279 | WM-290 | WM-70 | WM-109 | WM-17 | WM-420 | WM-449 |
| 42 | WM-343 | WM-283 | WM-342 | WM-366 | WM-545 | WM-302 | WM-203 | WM-184 | WM-74 |
| 43 | WM-341 | WM-685 | WM-471 | WM-472 | WM-675 | WM-587 | WM-83 | WM-67 | WM-261 |
| 44 | WM-339 | WM-66 | WM-674 | WM-420 | WM-446 | WM-375 | WM-412 | WM-66 | WM-467 |
| 45 | WM-55 | WM-55 | WM-120 | WM-147 | WM-120 | WM-131 | WM-96 | WM-391 | WM-237 |
| 46 | WM-56 | WM-650 | WM-20 | WM-55 | WM-257 | WM-706 | WM-74 | WM-340 | WM-262 |
| 47 | WM-48 | WM-307 | WM-287 | WM-669 | WM-466 | WM-398 | WM-457 | WM-428 | WM-295 |
| 48 | WM-38 | WM-278 | WM-83 | WM-357 | WM-347 | WM-309 | WM-431 | WM-198 | WM-288 |
| 49 | WM-138 | WM-342 | WM-154 | WM-429 | WM-153 | WM-55 | WM-340 | WM-312 | WM-384 |
| 50 | WM-310 | WM-429 | WM-128 | WM-279 | WM-38 | WM-488 | WM-49 | WM-152 | WM-37 |

RSFFSFLGEAFDGARDMWRAYSDMREANYIGSDKYFHARGNYDAAKRGPGGVWAAEAISDARENIQRFFGHGAEDSLADQAANEWGRSGKDPNHFRPAGLPEKY

2803
SAA 42-67 (2802.1)

3168
SAA 69-97 (3167.3)

3277
SAA 39-68 (3276.6)

3552
SAA 38-70 (3552)

3897
SAA 64-98 (3897.2)

4300
SAA 54-93 (4302.5)

4490
SAA 53-93 (4489)

4655
SAA 5-44 (4655.0)

5927
SAA 32-85 (5925.3)

6874
SAA 26-88 (6873.3)

7776
SAA 1-68 (7774.6)

7941
SAA 18-88 (7939.5)

8152
SAA 25-98 (8150)

8952
SAA 6-85 (8950)

9233
SAA 16-97 (9235)

10300
SAA 6-97 (10299.1)

10866
SAA 4-101 (10871.8)

10851
SAA 5-102 (10853.7)

Figure 5

Protein Profile of Selected Samples Q Fraction 1 WCX2

Protein Profile of Selected Samples
Q Fraction 1 WCX2

Protein Profile of Selected Samples
Q Fraction 2 WCX2

Protein Profile of Selected Samples
Q Fraction 2 WCX2

Protein Profile of Selected Samples
Q Fraction 4 WCX2

Protein Profile of Selected Samples
Q Fraction 4 WCX2

Protein Profile of Selected Samples
Q Fraction 5 WCX2

Protein Profile of Selected Samples
Q Fraction 5 WCX2

Protein Profile of Selected Samples
Q Fraction 6 WCX2

Protein Profile of Selected Samples
Q Fraction 6 WCX2

Protein Profile of Selected Samples
Q Fraction 2 IMAC-Cu(II)

Protein Profile of Selected Samples
Q Fraction 2 IMAC-Cu(II)

Protein Profile of Selected Samples
Q Fraction 2 IMAC-Cu(II)

Protein Profile of Selected Samples
Q Fraction 2 IMAC-Cu(II)

Protein Profile of Selected Samples
Q Fraction 3 IMAC-Cu(II)

Protein Profile of Selected Samples
Q Fraction 3 IMAC-Cu(II)

Protein Profile of Selected Samples
Q Fraction 5 IMAC-Cu(II)

Protein Profile of Selected Samples
Q Fraction 5 IMAC-Cu(II)

Protein Profile of Selected Samples
Q Fraction 5 IMAC-Cu(II)

Protein Profile of Selected Samples
Q Fraction 6 IMAC-Cu(II)

Protein Profile of Selected Samples
Q Fraction 6 IMAC-Cu(II)

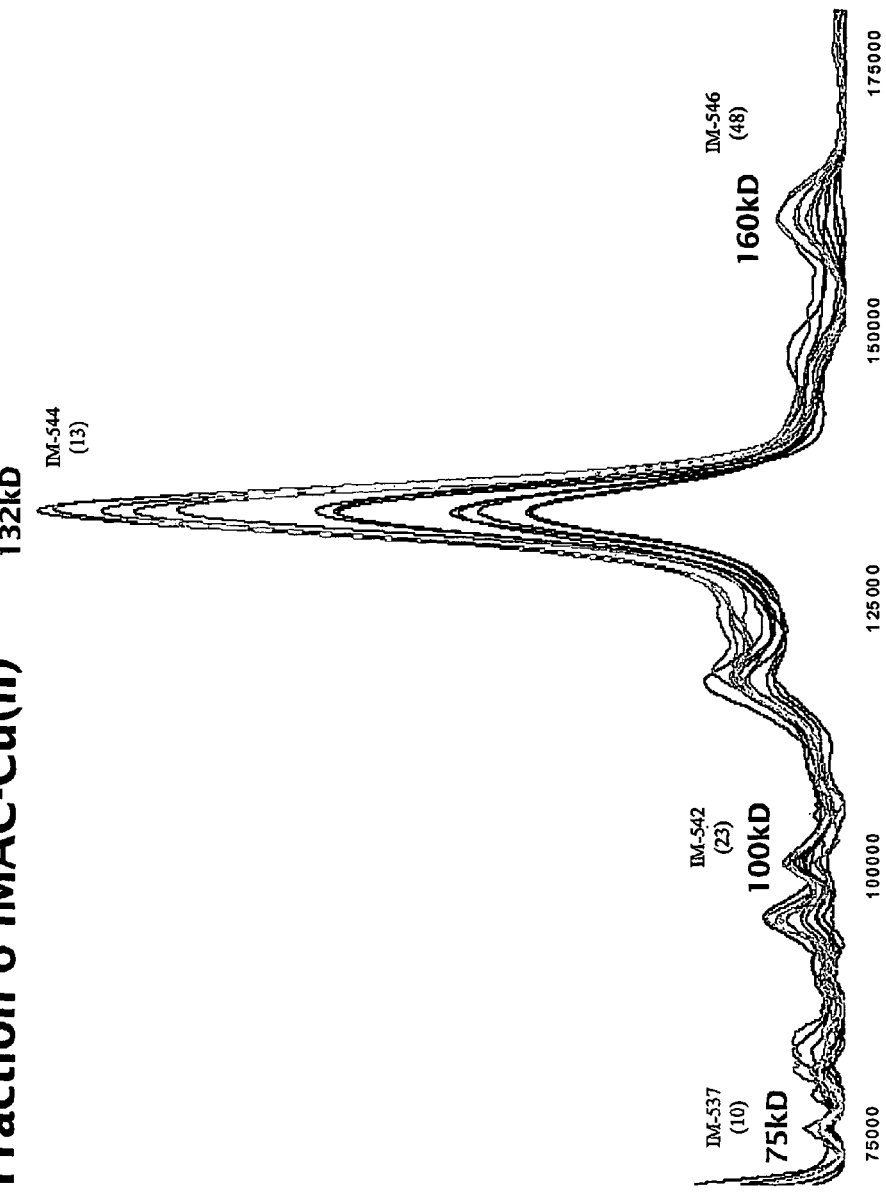

SERUM BIOMARKERS IN LUNG CANCER

BACKGROUND OF THE INVENTION

The present invention relates generally to the field of serum biomarkers in lung carcinoma. More particularly, the invention relates to serum biomarkers that can distinguish lung cancer from normal.

Lung cancer is the leading cause of cancer death worldwide, resulting in 150,000 deaths per year in the United States. The mortality rate from lung cancer is greater than the combined mortality from breast, prostate and colorectal cancers. On the basis of morphology, lung cancer can be broadly classified into four main categories namely, adenocarcinoma, squamous cell carcinoma, large cell undifferentiated carcinoma and small cell carcinoma. In Hong Kong from 1990 to 1996, the proportions for adenocarcinoma, squamous cell carcinoma, large cell undifferentiated carcinoma and small cell carcinoma are 45.5%, 27.5%, 4.7% and 10.3% respectively. Both squamous cell carcinoma and small cell carcinoma are strongly associated with a smoking history.

Adenocarcinoma, squamous cell carcinoma, and large cell undifferentiated carcinoma are usually referred as "non-small cell carcinoma." They are relatively chemo-resistant, and hence the mainstay of treatment is surgery. By contrast, small cell carcinoma has a higher propensity for distant metastases and is mainly treated by chemotherapy.

Biopsy can be used to diagnose lung cancer, but it is an invasive procedure and, therefore, less than desirable. Other diagnostic methods for lung cancer include ultrasound and computed tomography (CT) scan.

It would be highly desirable to have a biomarker or combination of biomarkers capable of distinguishing between lung cancer and normal cells. In addition, a simple test could aid in tracking treatment progress and even identify molecular targets for therapy. The literature on lung cancer diagnosis has not disclosed heretofore such a biomarker or combination of biomarkers, however.

SUMMARY OF THE INVENTION

In accordance with the present invention, biomarkers and combinations of biomarkers are used to identify lung cancer. The method successfully distinguishes between lung cancer and normal states, and can be used to identify the particular type of lung cancer. In one embodiment, a method for qaulifying lung carcinoma status in a subject (e.g., a patient) comprises analyzing a biological sample from the subject for one or more of the top 50 biomarkers as shown in FIG. 2 or FIGS. 4A and 4B. Thus, to assess overall lung cancer risk versus normal, a biomarker is selected from the group consisting of (A) IM-522, IM-273, IM-520, IM-519, IM-454, IM-507, IM-521, IM-148, IM-266, IM-537, IM-471, IM-510, IM-544, IM-474, IM-155, IM-157, IM-176, IM-445, IM-177, IM-440, IM-468, IM-438, IM-547, IM-359, IM-436, IM-106, IM-455, IM-444, IM-158, IM-265, IM-50, IM-159, IM-156, IM-439, IM-157, IM-508, IM-514, IM-478, IM-473, IM-360, IM-435, IM-150, IM-151, IM-110, IM-51, IM-163, IM-437, IM-546, IM-153, and IM-268, or (B) WM-61, WM-447, WM-446, WM-133, WM-119, WM-278, WM-134, WM-363, WM-282, WM-362, WM-120, WM-290, WM-65, WM-277, WM-70, WM-369, WM-17, WM-473, WM-47, WM-203, WM-276, WM-279, WM-62, WM-366, WM-456, WM-428, WM-384, WM-287, WM-420, WM-292, WM-431, WM-455, WM-20, WM-340, WM-105, WM-389, WM-63, WM-354, WM-450, WM-466, WM-296, WM-343, WM-341, WM-339, WM-55, WM-66, WM-48, WM-38, WM-138, and WM-310, wherein the biomarker is differentially present in samples of a subject with lung cancer and a so-called "normal" subject that is free of lung cancer.

More preferably, one or more of the top 15 biomarkers as shown in FIG. 2 or FIGS. 4A and 4B is used to qualify lung cancer status. Thus, for assessing overall lung cancer status versus normal, the protein is selected from the group consisting of (A) IM-522, IM-273, IM-520, IM-519, IM-454, IM-507, IM-521, IM-148, IM-266, IM-537, IM-471, IM-510, IM-544, IM-474, IM-155, IM-471, IM-510, IM-544, IM-474, and IM-155, or (B) WM-61, WM-447, WM-446, WM-133, WM-119, WM-278, WM-134, WM-363, WM-282, WM-362, WM-120, WM-290, WM-65, WM-277, WM-70.

Still more preferably, one or more of the top 5 biomarkers as shown in FIG. 2 or FIGS. 4A and 4B is used to qualify lung cancer status. In this instance, for overall lung cancer status versus normal, the biomarker is selected from the group consisting of (A) IM-522, IM-273, IM-520, IM-519, and IM-454, or
(B) WM-61, WM-447, WM-446, WM-133, and WM-119.

In one embodiment, the method measures a plurality of biomarkers. The plurality of biomarkers can be measured simultaneously.

Biomarkers that, by themselves, are able to identify lung cancer include the WM-446 and WM-447 protein biomarkers, and these are particularly preferred.

The present invention also provides a method for qualifying lung cancer status in a subject (e.g., a patient), comprising (A) providing a spectrum generated by subjecting a biological sample from said subject to mass spectroscopic analysis that includes profiling on a chemically-derivatized affinity surface, and (B) putting the spectrum through pattern-recognition analysis that is keyed to at least one peak selected from the top 50 biomarkers as shown in FIG. 2 or FIGS. 4A and 4B. Thus, for qualifying overall lung cancer status, the biomarker is selected from the, group consisting of (i) IM-522, IM-273, IM-520, IM-519, IM-454, IM-507, IM-521, IM-148, IM-266, IM-537, IM-471, IM-510, IM-544, IM-474, IM-155, IM-157, IM-176, IM-445, IM-177, IM-440, IM-468, IM-438, IM-547, IM-359, IM-436, IM-106, IM-455, IM-444, IM-158, IM-265, IM-50, IM-159, IM-156, IM-439, IM-157, IM-508, IM-514, IM-478, IM-473, IM-360, IM-435, IM-150, IM-151, IM-110, IM-51, IM-163, IM-437, IM-546, IM-153, and IM-268, or (B) WM-61, WM-447, WM-446, WM-133, WM-119, WM-278, WM-134, WM-363, WM-282, WM-362, WM-120, WM-290, WM-65, WM-277, WM-70, WM-369, WM-17, WM-473, WM-47, WM-203, WM-276, WM-279, WM-62, WM-366, WM-456, WM-428, WM-384, WM-287, WM-420, WM-292, WM-431, WM-455, WM-20, WM-340, WM-105, WM-389, WM-63, WM-354, WM-450, WM-466, WM-296, WM-343, WM-341, WM-339, WM-55, WM-66, WM-48, WM-38, WM-138, and WM-310.

For assessing the overall lung cancer status, the pattern-recognition analysis may, for example, be paired to a pair of peaks selected from the group consisting of (A) IM-266 and IM-474, IM-266 and IM-38, IM-266 and IM-454, IM-266 and IM-522, IM-266 and IM-544, IM-266 and IM-471, IM-474 and IM-151, IM-474 and IM-156, IM-474 and IM-544, IM-474 and IM-38, IM-522 and IM-507, IM-522 and IM-156, and IM-522 and IM-440; or
(B) WM-447 and WM-59, WM-447 and WM-19, WM-447 and WM-118, WM-447 and WM-473, WM-19 and WM-59, WM-19 and WM-473, WM-19 and WM-369, WM-61 and WM-154, WM-61 and WM-369, WM-118 and WM-59 and WM-282 and WM-127.

More preferably, for assessing overall lung cancer status, the pattern-recognition analysis is keyed to a pair of peaks selected from the group consisting of
(A) IM-266 and IM-474, IM-266 and IM-544, and IM-156 and IM-522; or
(B) WM-447 and WM-59, WM-447 and WM-19, and WM-19 and WM-59.

Alternatively, the pattern-recognition analysis for assessing overall lung cancer status may be keyed to a triplet of peaks selected from the group consisting of
(A) IM-266, IM-454 and IM-474; and IM-266, IM-474 and IM-544; or
(B) WM-447, WM-19 and WM-473.

In other embodiments, the pattern-recognition analysis may be keyed to a combination of more than three peaks, more particularly to a combination of 4, 5 or 6 peaks, where the combination is selected from among the combinations shown in Tables 1 and 2 herein.

In each case, the biomarker is differentially present in samples of a subject with lung cancer and a normal subject.

The invention also contemplates a kit for detecting and diagnosing lung cancer, thereby to assess lung cancer status. Kits within the invention comprise, for example, (i) an adsorbent attached to a substrate that retains one or more of the biomarkers shown in FIG. 2 or FIGS. 4A and 4B, and (ii) instructions to detect the biomarker(s) by contacting a sample with the adsorbent and detecting the biomarker(s) retained by the adsorbent. An inventive kit may further comprise a washing solution and/or instructions for making a washing solution. The kits may include more than type of adsorbent, each present on a different substrate, e.g., on a WCX and IMAC biochip. In addition, the kits may comprise one or more containers with biomarker samples, to be used as standard(s) for calibration. The substrate comprising the adsorbent may be designed to engage a probe interface and, hence, function as a probe in gas phase ion spectrometry, preferably mass spectrometry. Alternatively, the kit may further comprise a second substrate adapted to engage the probe interface, on which the substrate comprising the adsorbent is mounted.

The method and kit according to the invention produce an article of manufacture in which one or more biomarkers according to the invention are bound to an adsorbent, optionally contacted with a matrix or energy absorbing molecule.

The present invention also provides software for qualifying lung carcinoma status in a subject, comprising an algorithm for analyzing data extracted from a spectrum generated by mass spectroscopic analysis of a biological sample taken from the subject, wherein said data relates to one or more biomarkers according to the invention. In one embodiment, the algorithm carries out a pattern-recognition analysis that is keyed to data relating to at least one of the biomarkers. In another embodiment, the algorithm comprises classification tree analysis that is keyed to data relating to at least one of the biomarkers. In yet another embodiment, the algorithm comprises an artificial neural network analysis that is keyed to data relating to at least one of the biomarkers.

In certain embodiments, the present invention provides methods and kits that use serum amyloid a protein or a fragment thereof to qualify lung carcinoma status in a subject. In one of these embodiments, the serum amyloid a biomarker has an apparent molecular weight of about 2803, 3168, 3277, 3552, 3897, 4300, 4490, 4655, 5927, 6874, 7776, 7941, 8152, 8952, 9233, 10300, 10866, or 10851 Daltons. In another embodiment, the serum amyloid a biomarker has an apparent molecular weight of about 3168, 3277, 3552, 3897, 4300, 4490, 4655, 7776, 7941, 8152, 8952, or 10851 Daltons. In yet another embodiment, the serum amyloid a biomarker has an apparent molecular weight of about 11.5 to 11.7 kD.

BRIEF DESCRIPTION OF THE DRAWINGS

FIGS. 1A-1D show all biomarkers identified with a Cu(II) IMAC3 ProteinChip® array format.
FIG. 2 shows the top 50 biomarkers identified with a Cu(II) IMAC3 ProteinChip® array format.
FIGS. 4A and 4B show the top 50 biomarkers identified with a WCX ProteinChip® array format.
FIG. 5 shows fragments of serum amyloid A (SAA) that are biomarkers according to the present invention.
FIGS. 17-28 are spectra from IMAC chips in which all of the top 15 WCX marker peaks are labeled, along with various other peaks from among the top 50 IMAC peaks. Blue shows spectra from lung cancer patients and gray shows normals.

DETAILED DESCRIPTION OF THE PREFERRED EMBODIMENTS

Figure 3C:
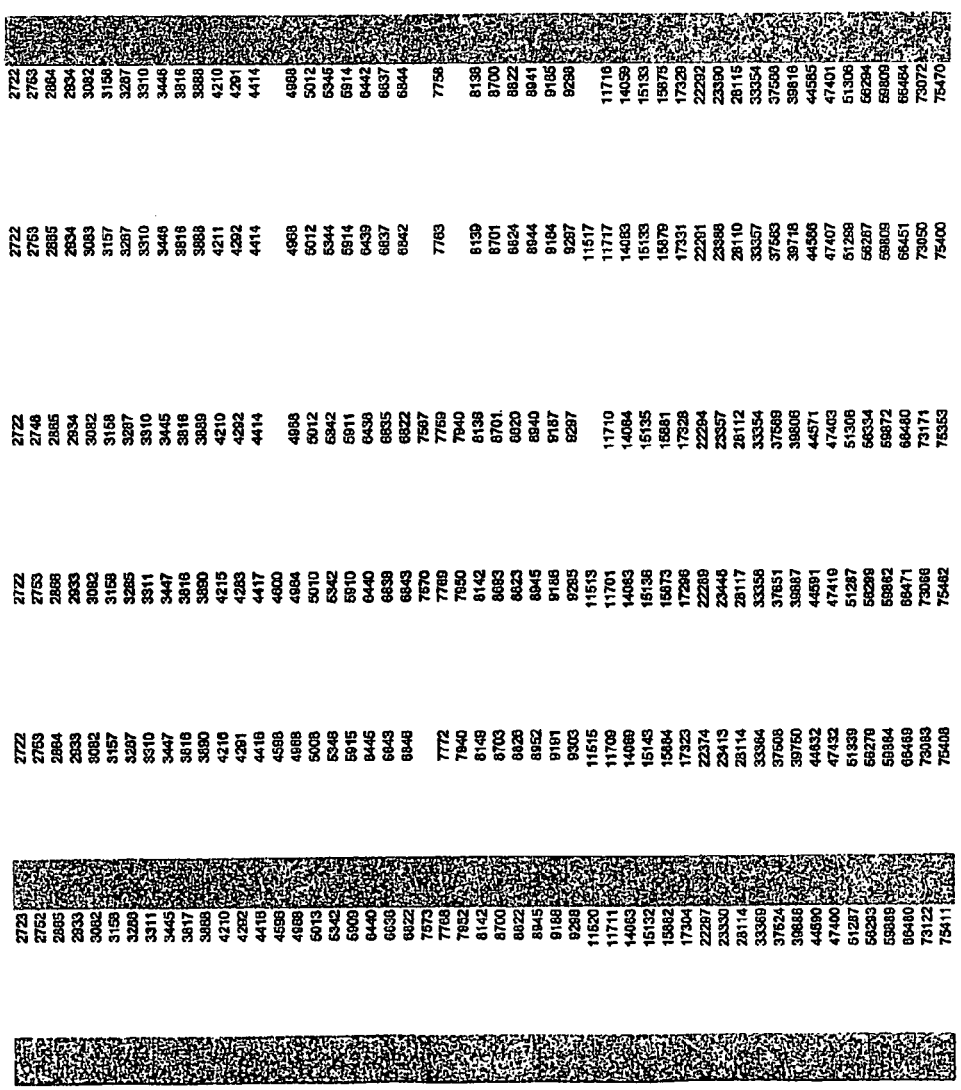
FIGS. 3A-3O show all biomarkers identified with a WCX ProteinChip® array format.
Figure 3E:
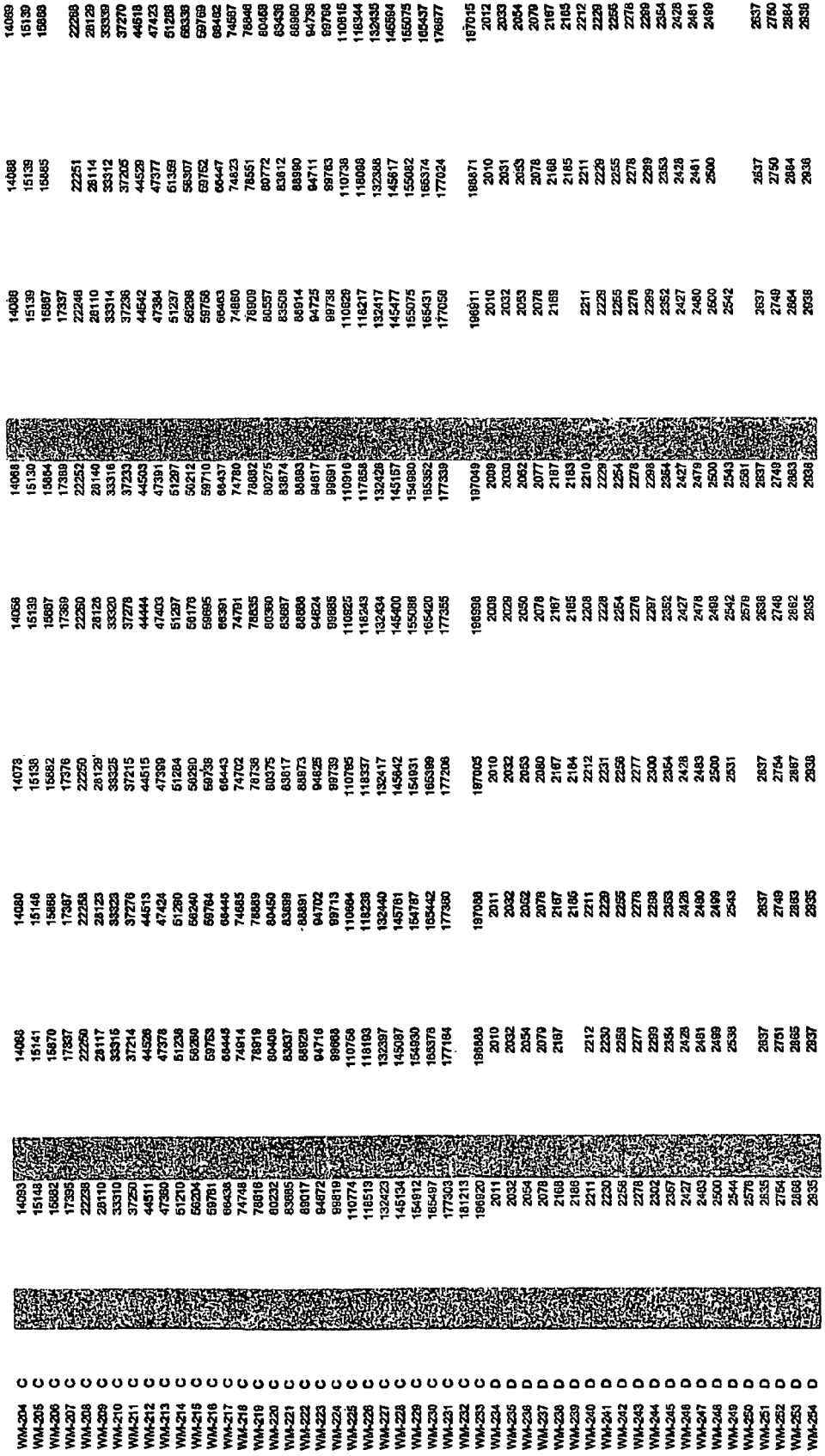
Figure 3K:
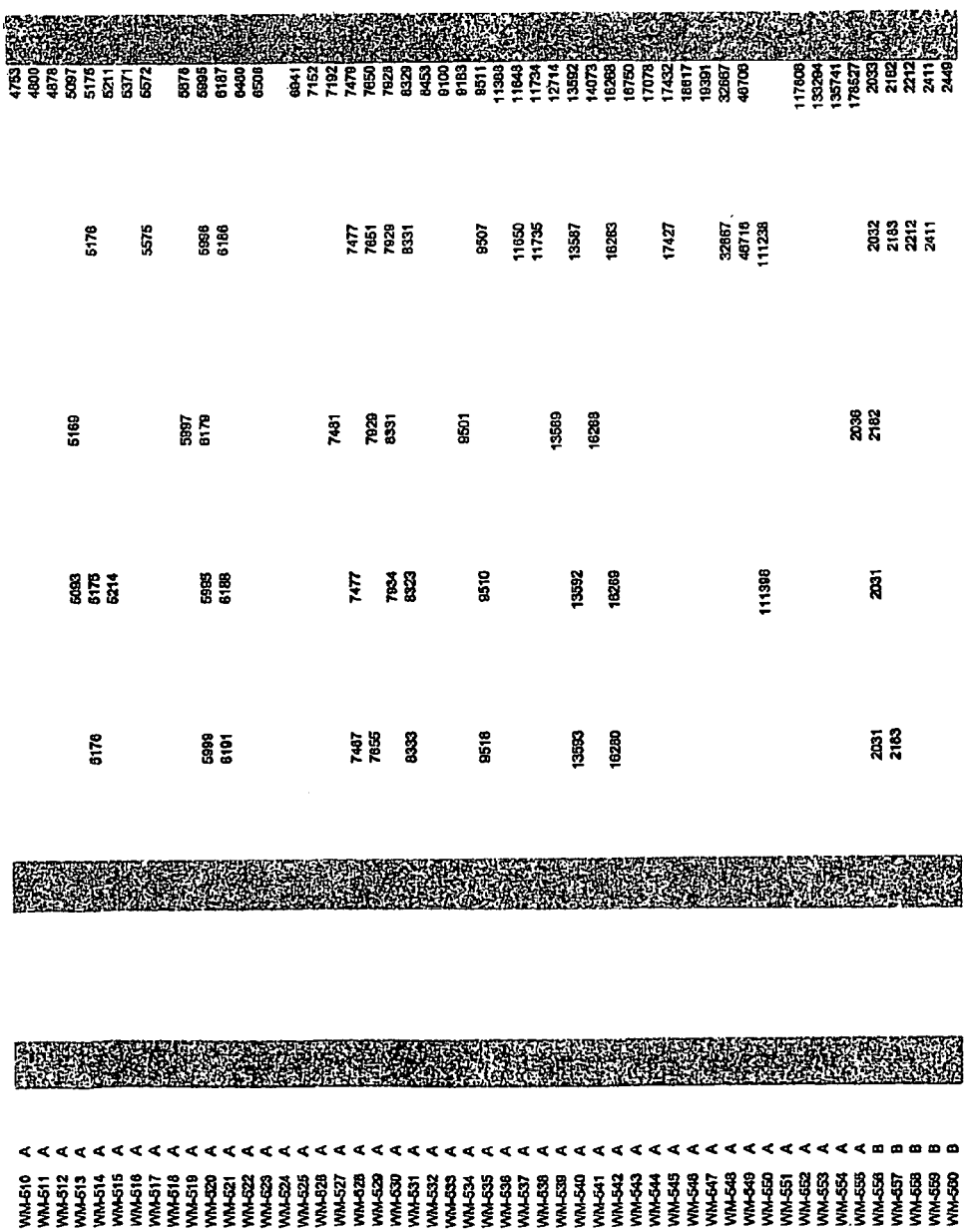

In accordance with the present invention, a series of biomarkers associated with lung cancer has been discovered. In the present context, a biomarker is an organic biomolecule, particularly a polypeptide or protein, which is differentially present in a sample taken from a subject having lung cancer as compared to a comparable sample taken from a normal subject. A biomarker also may be differentially present in a sample taken from a subject with one type of lung cancer, e.g. small cell carcinoma, as compared to a comparable sample taken from a subject with a different type of lung cancer, e.g., adenocarcinoma or squamous cell carcinoma, or differentially present at different stages of a type of lung cancer. A biomarker is differentially present in samples taken from two groups of subjects if it is present at an elevated level or a decreased level in samples of the first group as compared to samples of the second group. More particularly, a biomarker is a polypeptide that is characterized by an apparent molecular weight, as determined by mass spectrometry, and that is present in samples from lung cancer subjects in an elevated or decreased level, as compared to subjects that do not have lung cancer. A biomarker is differentially present between two sets of samples if the amount of the biomarker in one sample set differs in a statistically significant way ($p<0.01$) from the amount of biomarker in the other sample set.

The biomarkers of the invention can be used to assess lung cancer status in a subject. For example, they are capable of identifying lung cancer and successfully distinguishing it from normal subjects, thereby providing a way of diagnosing the presence or absence of lung cancer, including the presence or absence of a particular kind of lung cancer. In addition, the biomarkers are useful in assessing the risk of developing lung cancer, in staging of lung cancer and in assessing the effectiveness of treatment. Thus, "lung cancer status" in the context of the present invention includes, inter alia, the presence or absence of disease, the risk of developing disease, the stage of the disease, and the effectiveness of treatment of disease. Based on this status, further procedures may be indicated, including additional diagnostic tests or therapeutic procedures or regimens, such as endoscopy, biopsy, surgery, chemotherapy, immunotherapy, and radiation therapy.

In some instances, a single biomarker is capable of identifying lung cancer with a sensitivity or specificity of at least 85%, whereas, in other instances, a combination or plurality of biomarkers is used to obtain a sensitivity or specificity of at least 85%. The biomarkers and combinations of biomarkers thus can be used to qualify lung cancer status in a subject or patient.

The biomarkers according to the invention are present in serum. The biological sample used according to the present invention, however, need not be a serum sample. Thus, a biological sample for qualifying lung cancer status may be a serum, plasma or blood sample, although serum samples are preferred.

All of the biomarkers are characterized by molecular weight. A list of all the biomarkers obtained with the Cu(II) IMAC3 ProteinChip® array (Ciphergen Biosystems, Inc., Fremont, Calif., USA) is provided in FIGS. 1A-1D, and FIG. 2 lists the top 50 biomarkers that distinguish between lung cancer and normal subjects that are identified by Cu(II) IMAC3 protocol described herein. FIGS. 3A-3O comprise a list of all the biomarkers obtained with the WCX2 ProteinChip® array, and FIGS. 4A and 4B comprise a ranking of the top 50 biomarkers that distinguish between (i) lung cancer and normal subjects, (ii) subjects with each of four types of lung cancer and normal subjects, and (iii) two types of lung cancer, e.g., adenocarcinoma versus squamous cell carcinoma, as identified by WCX2 protocol described herein.

The top 50 biomarkers were determined by decision tree analysis using Biomarker Patterns™ software from Ciphergen Biosystems, Inc. Biomarkers other than those within the top 50 also are useful in distinguishing between subjects with lung cancer and normal subjects and may, in particular, appear in decision trees with multiple nodes. In preferred embodiments, one or more of the top 15 biomarkers are used, and in even more preferred embodiments, one or more of the top 5 biomarkers are used.

In each of FIGS. 1A-1D and 3A-3O, the number in the first column is the biomarker identifier. Thus, the first row in FIGS. 1A-1D relates to biomarker IM-1, the second row relates to biomarker IM-2, and so forth ("IM-" denoting biomarkers identified with the IMAC chip). Similarly, the first row in FIGS. 3A-3O relates to biomarker WM-1 and the second row relates to biomarker WM-2 ("WM-" denoting biomarkers identified with the WCX2 chip). The number in the second column in FIGS. 1A-1D is the apparent molecular weight of the biomarker in daltons, as determined by mass spectrometry. In FIGS. 3A-3O, the apparent molecular weights for the biomarkers identified in the first column are reported in columns 3 through 11. The letter in the second column of FIGS. 1A-1D and the third column of FIGS. 3A-3O denotes the fraction in which the biomarker elutes in the protocol described herein; that is, biomarkers with an "A" elute in the first fraction, biomarkers with a "B" elute in the second fraction, and so forth. The fraction in which the biomarker elutes correlates with its pI, which biomarkers eluting at higher pH having a higher pI, and biomarkers eluting at lower pH having a lower pI.

Presenting the mass and affinity characteristics of a given biomarker within the invention, as in this description, characterizes that biomarker so as allow one to obtain and measure it, in accordance with the teachings herein. If desired, any of the biomarkers can be sequenced, in order to obtain an amino acid sequence, but this is not required to practice the present invention.

For example, a biomarker can be peptide mapped with a number of enzymes, such as trypsin and V8 protease, and the molecular weights of the digestion fragments can be used to search databases for sequences that match the molecular weights of the digestion fragments generated by the various enzymes. Alternatively, if the biomarkers are not proteins included in known databases, degenerate probes can be made based on the N-terminal amino acid sequence of the biomarker, which then are used to screen a genomic or cDNA library created from a sample from which the biomarker was initially detected. The positive clones can be identified, amplified, and their recombinant DNA sequences can be subcloned using techniques which are well known. Finally, protein biomarkers can be sequenced using protein ladder sequencing. Protein ladders can be generated by fragmenting the molecules and subjecting fragments to enzymatic digestion or other methods that sequentially remove a single amino acid from the end of the fragment. The ladder is then analyzed by mass spectrometry. The difference in masses of the ladder fragments identifies the amino acid removed from the end of the molecule.

Figure 6:
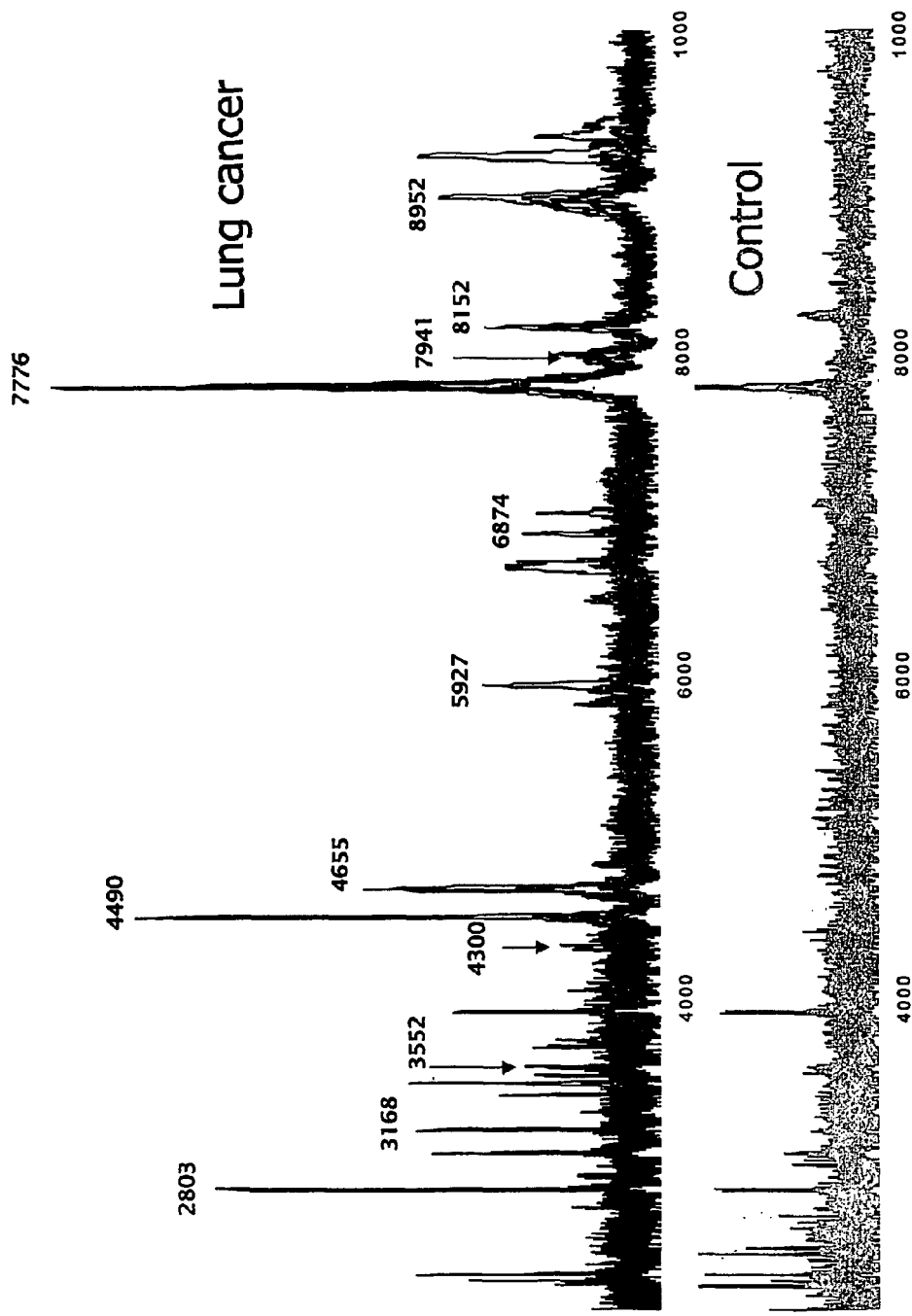
FIG. 6 shows identification of SAA biomarkers with an anti-SAA antibody.
Figure 7:
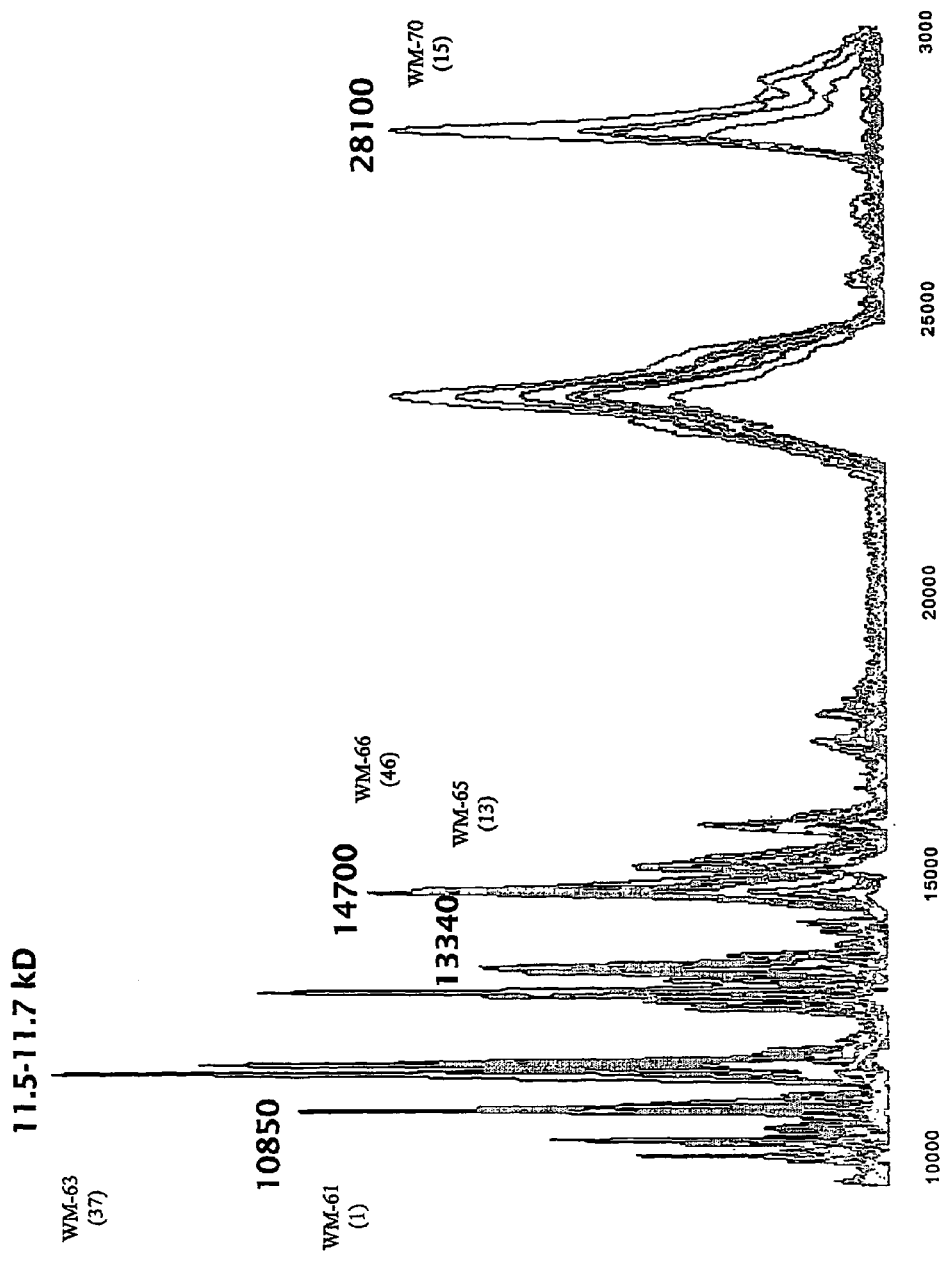
FIGS. 7-16 are spectra from WCX chips in which all of the top 15 WCX marker peaks are labeled, along with various other peaks from among the top 50 WCX peaks. Red shows spectra from lung cancer patients and gray shows normals.
Figure 8:
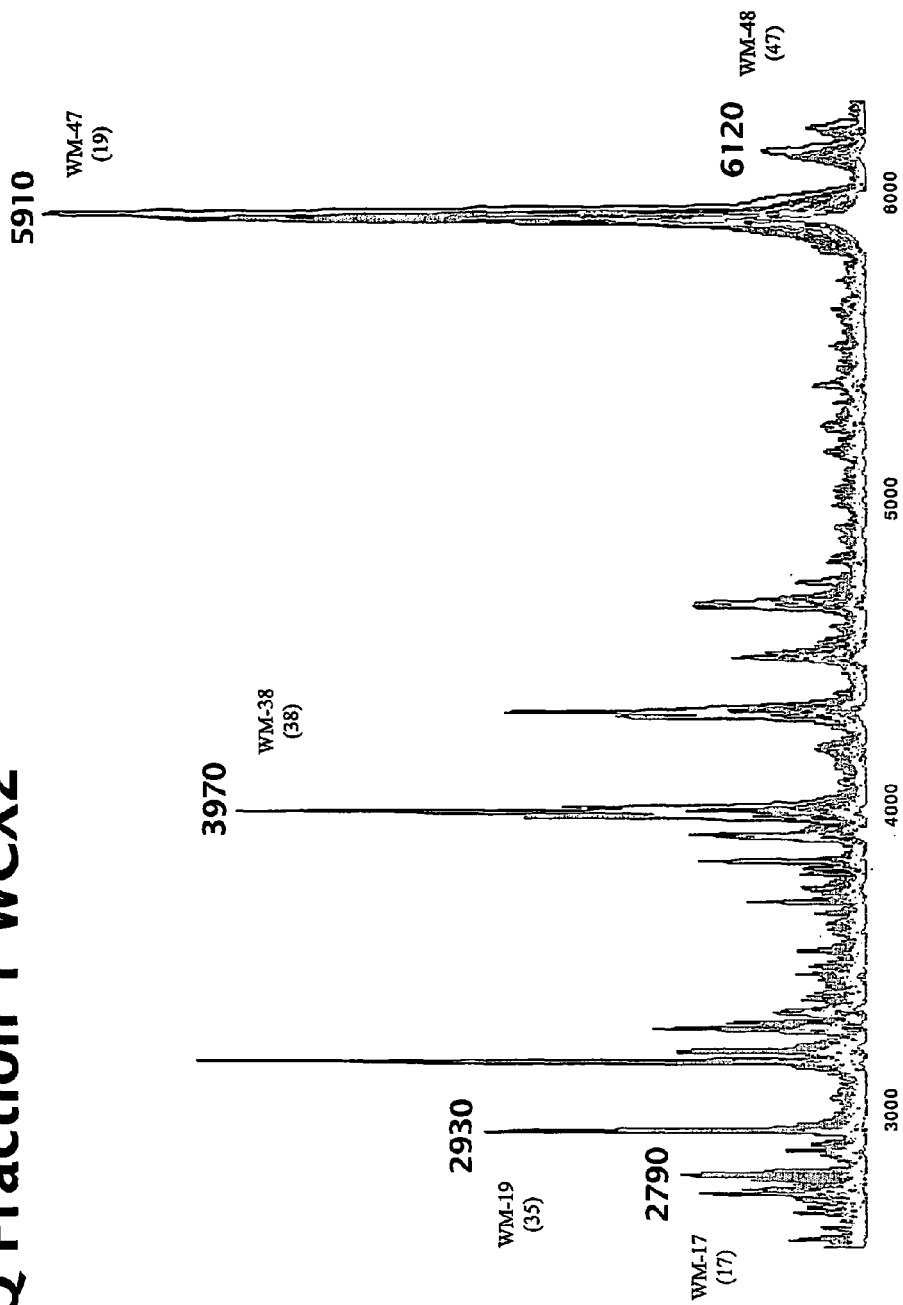
Figure 9:
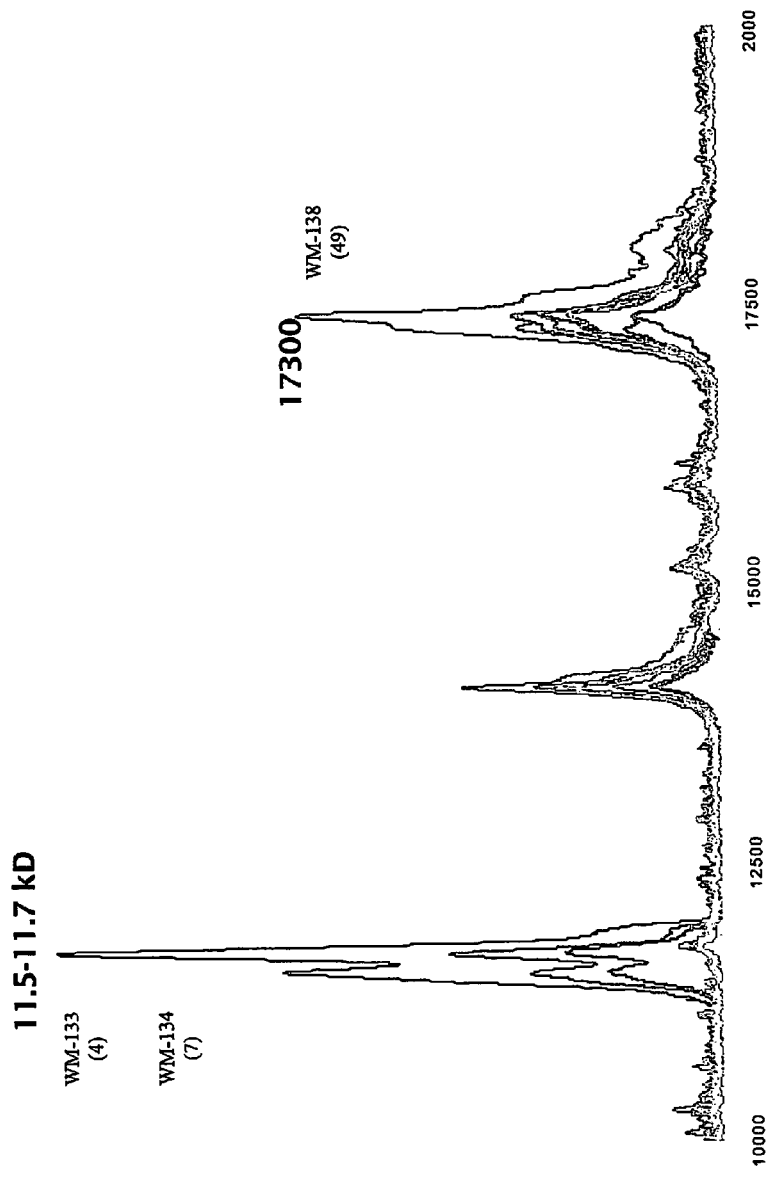
Figure 10:
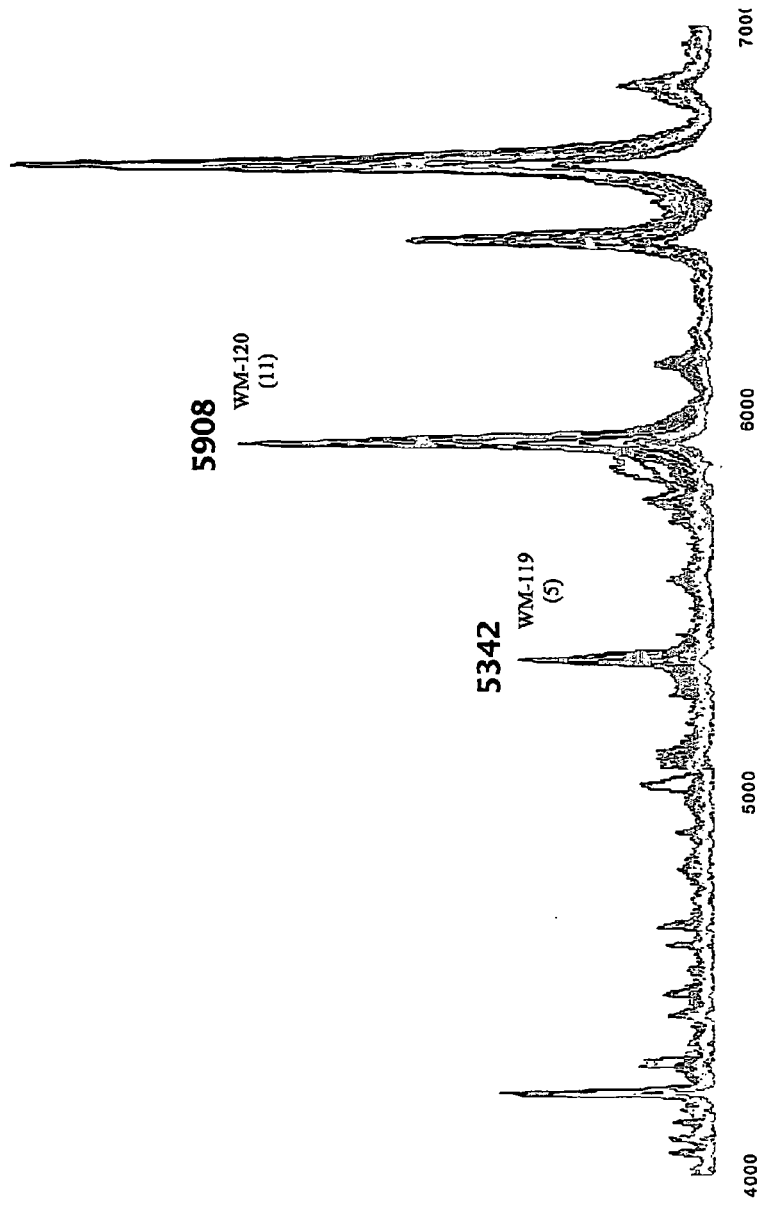
Figure 11:
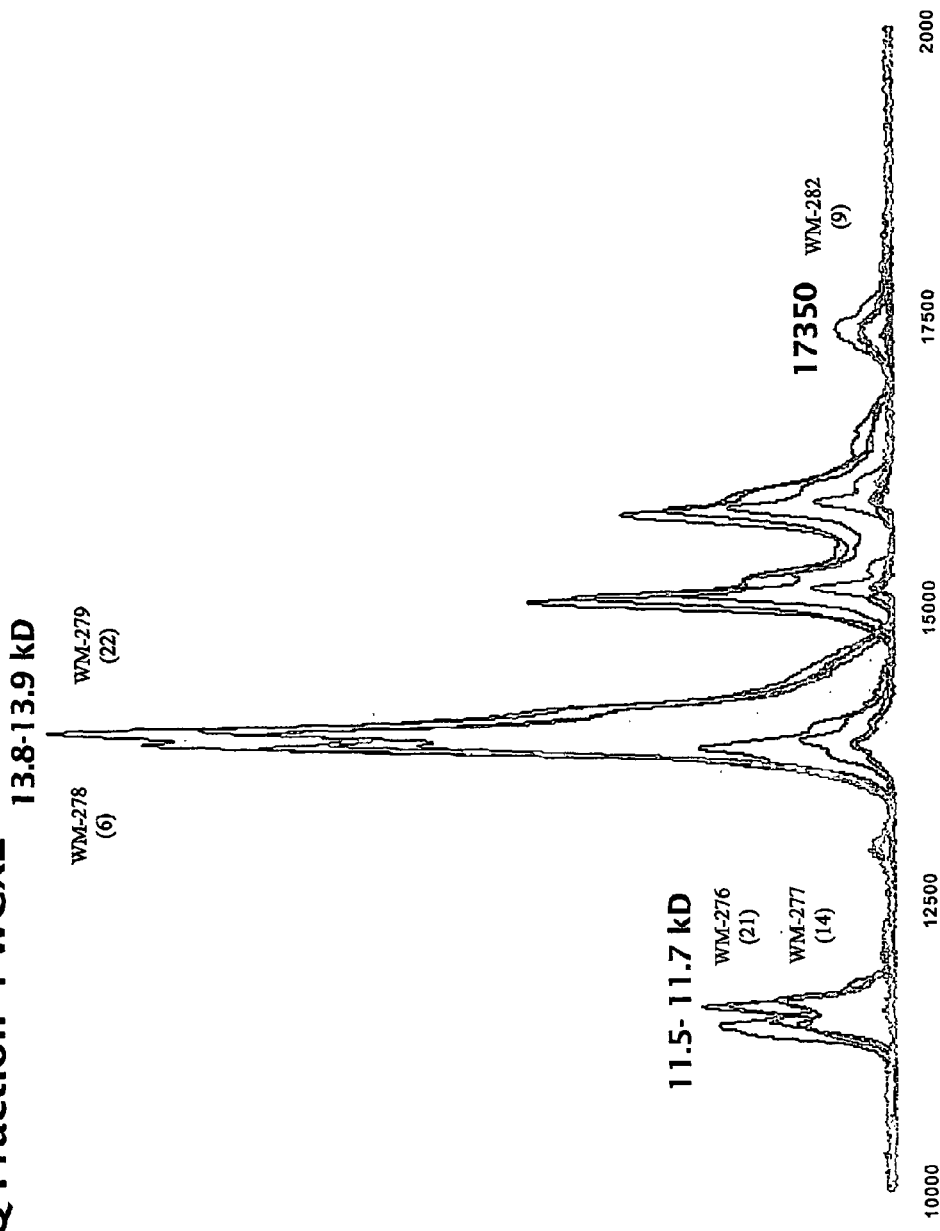
Figure 12:
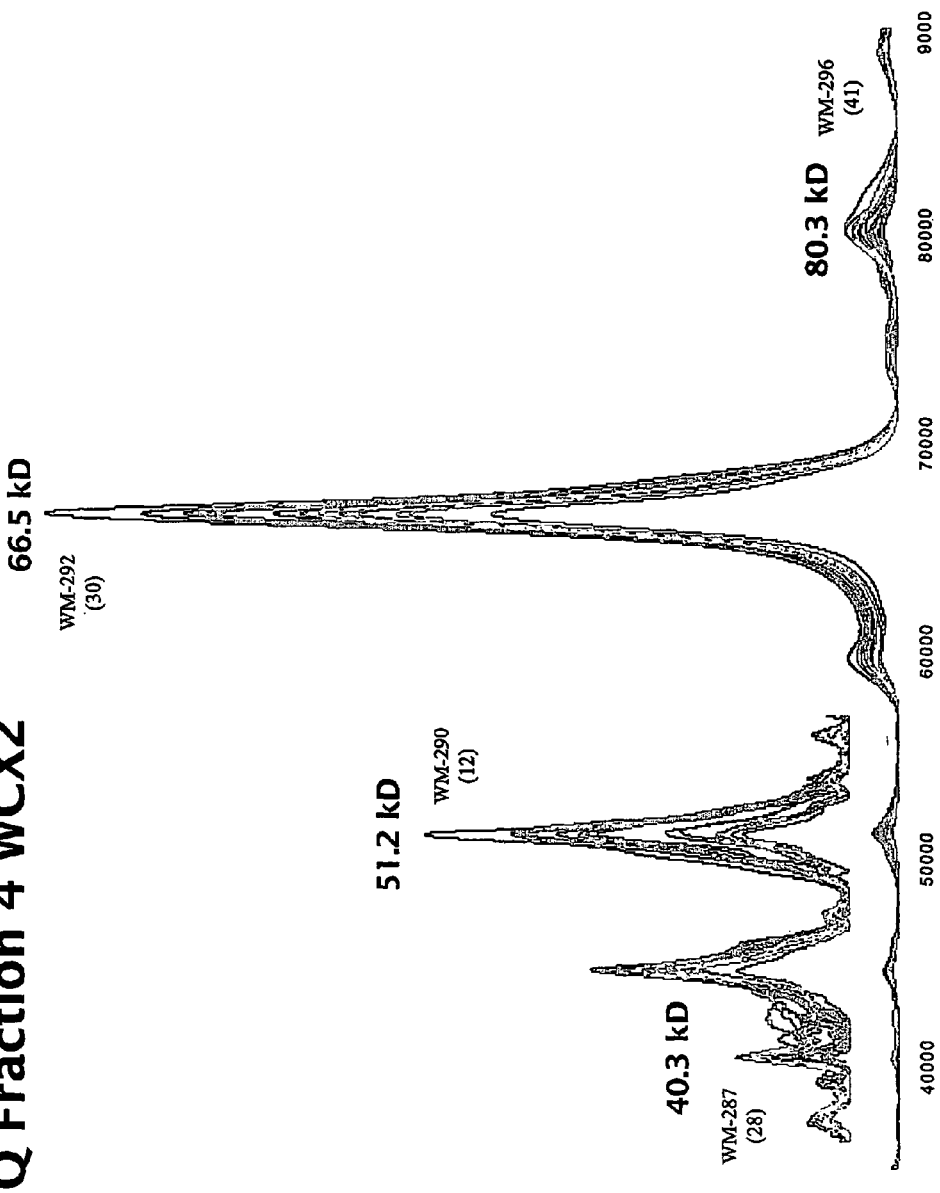
Figure 13:
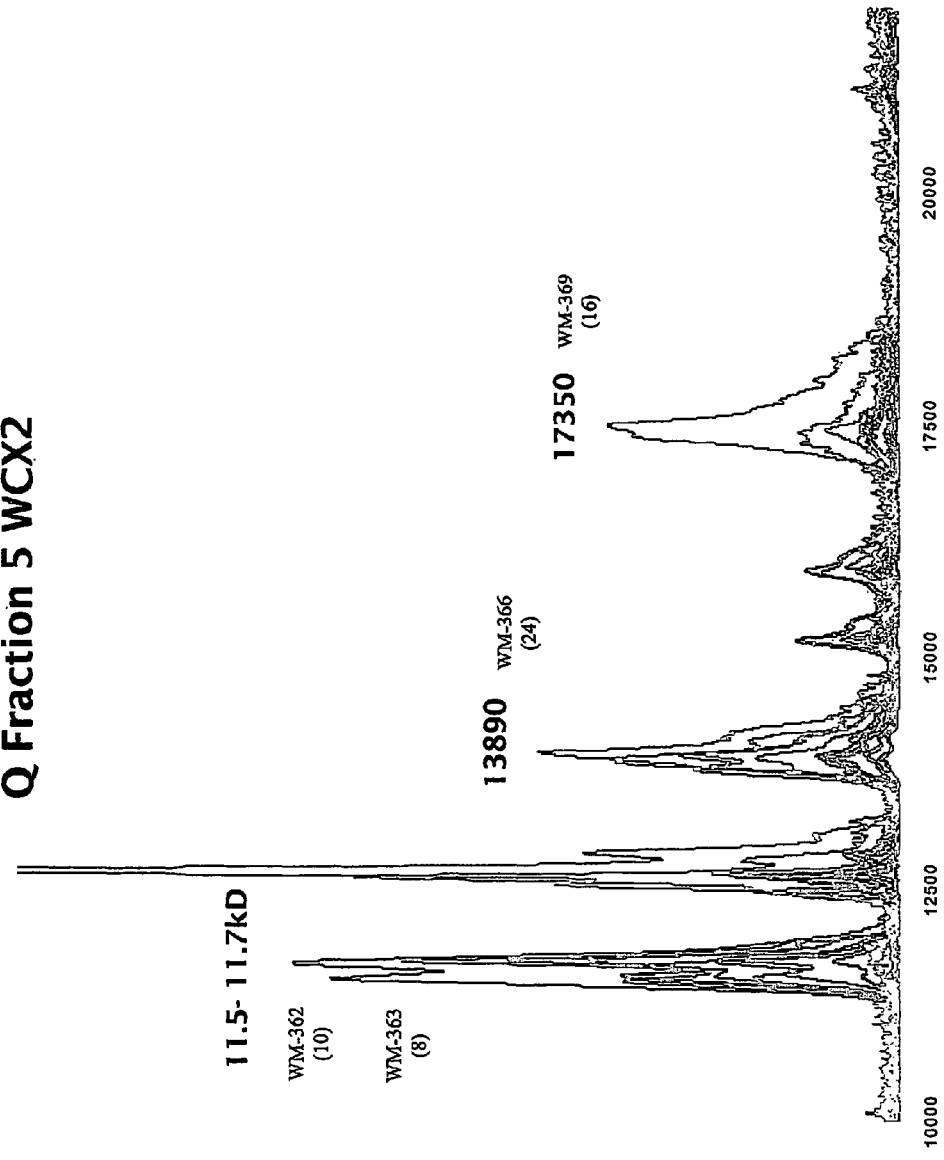
Figure 14:
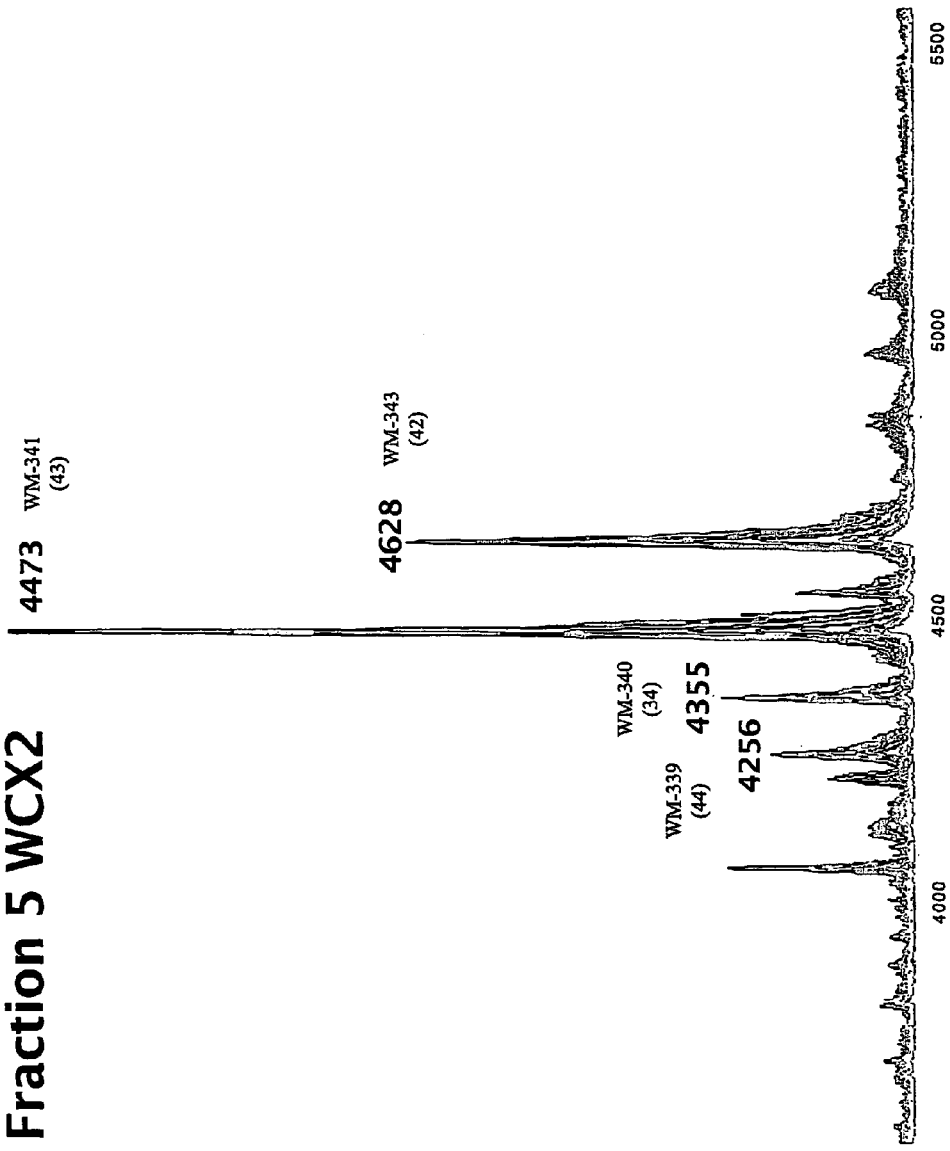
Figure 15:
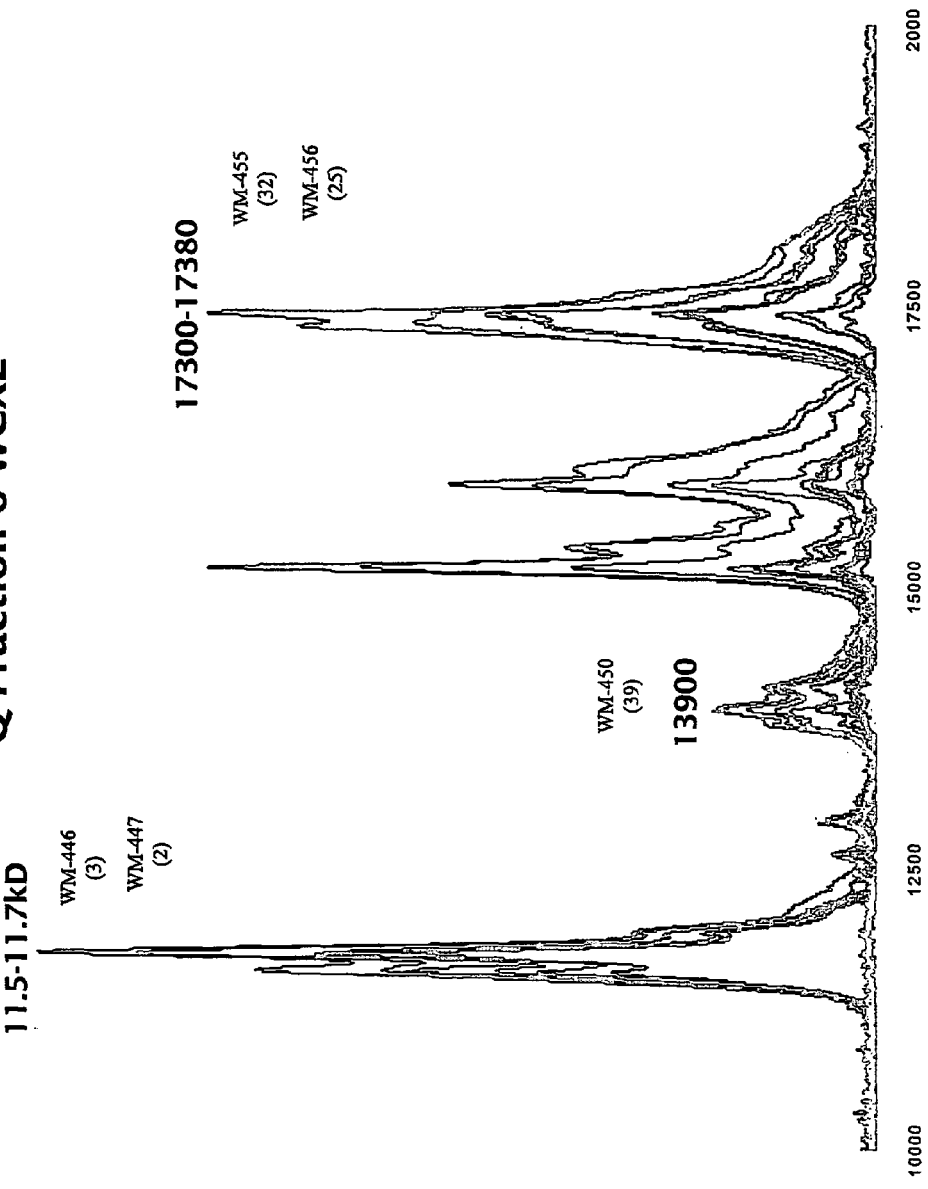
Figure 16:
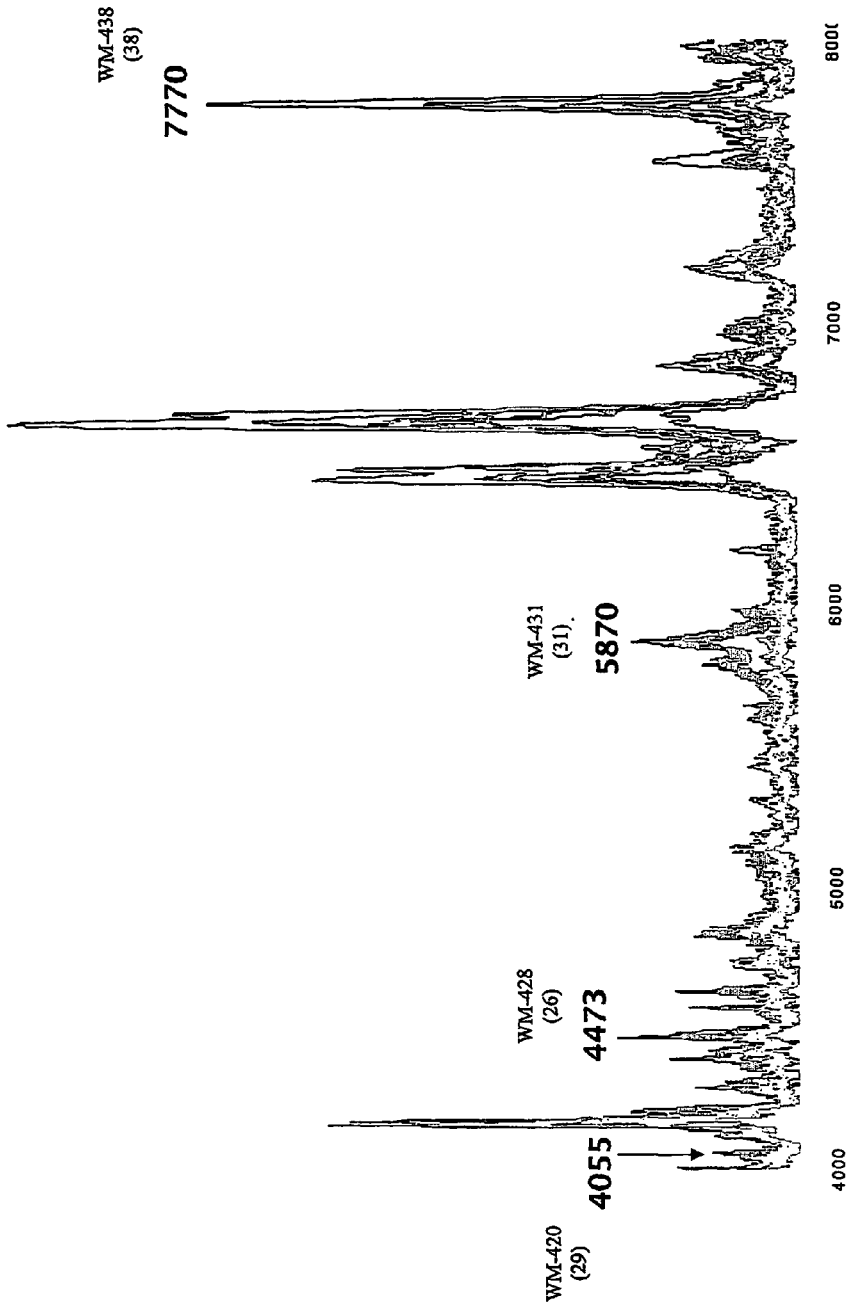
Figure 17:
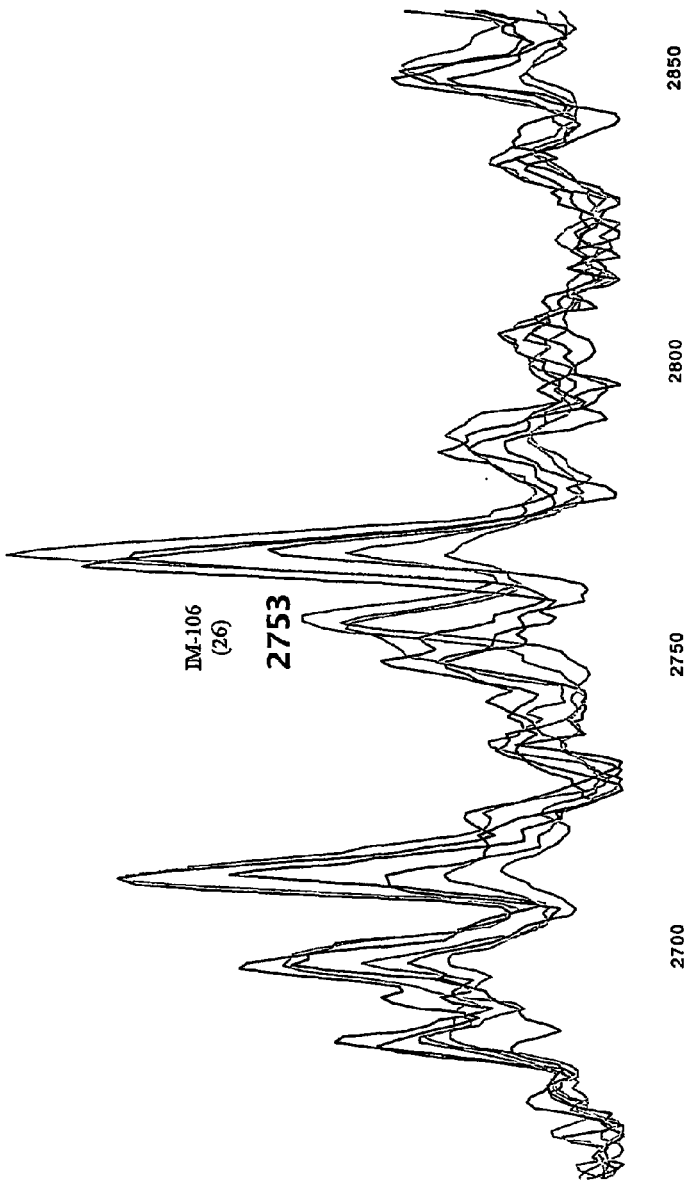
Figure 18:
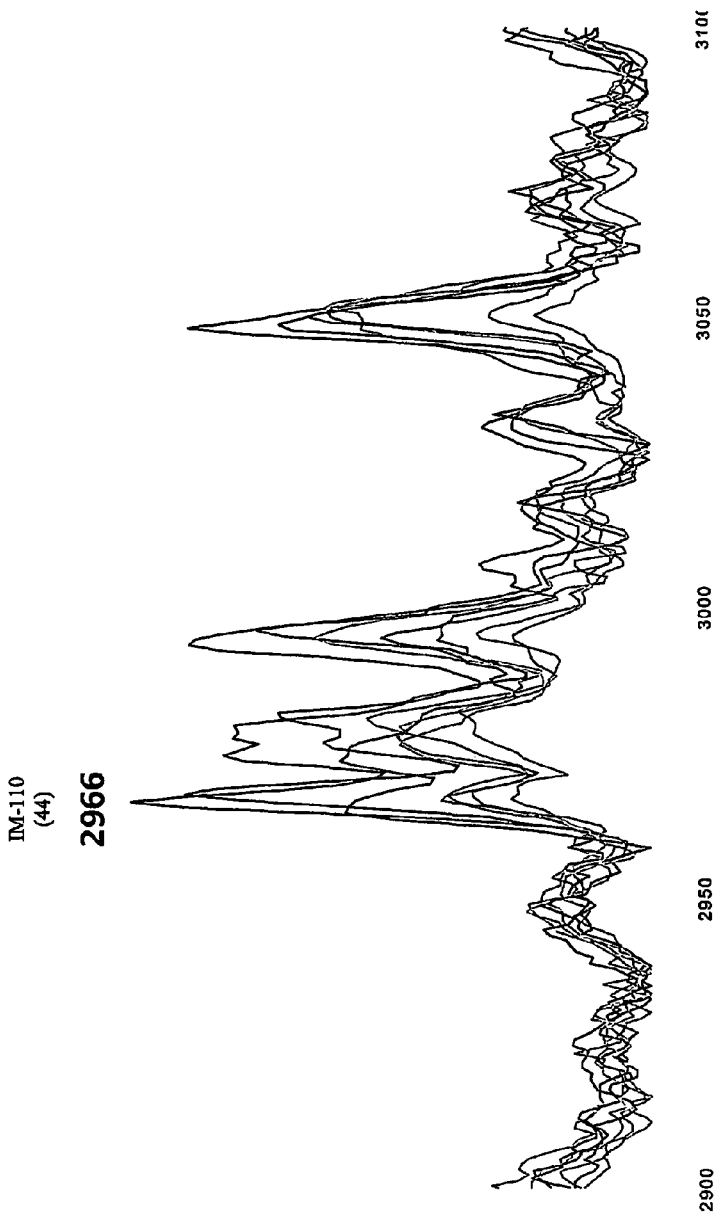
Figure 19:
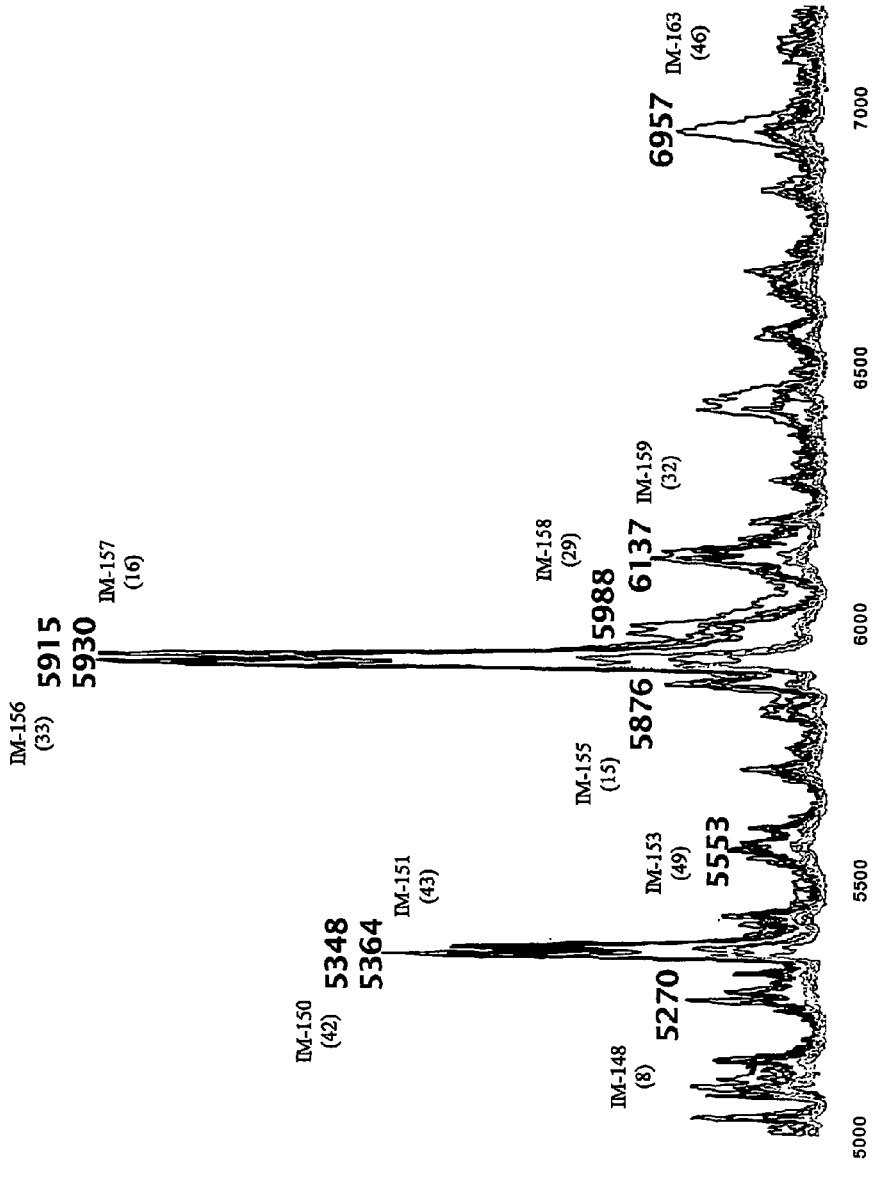
Figure 20:
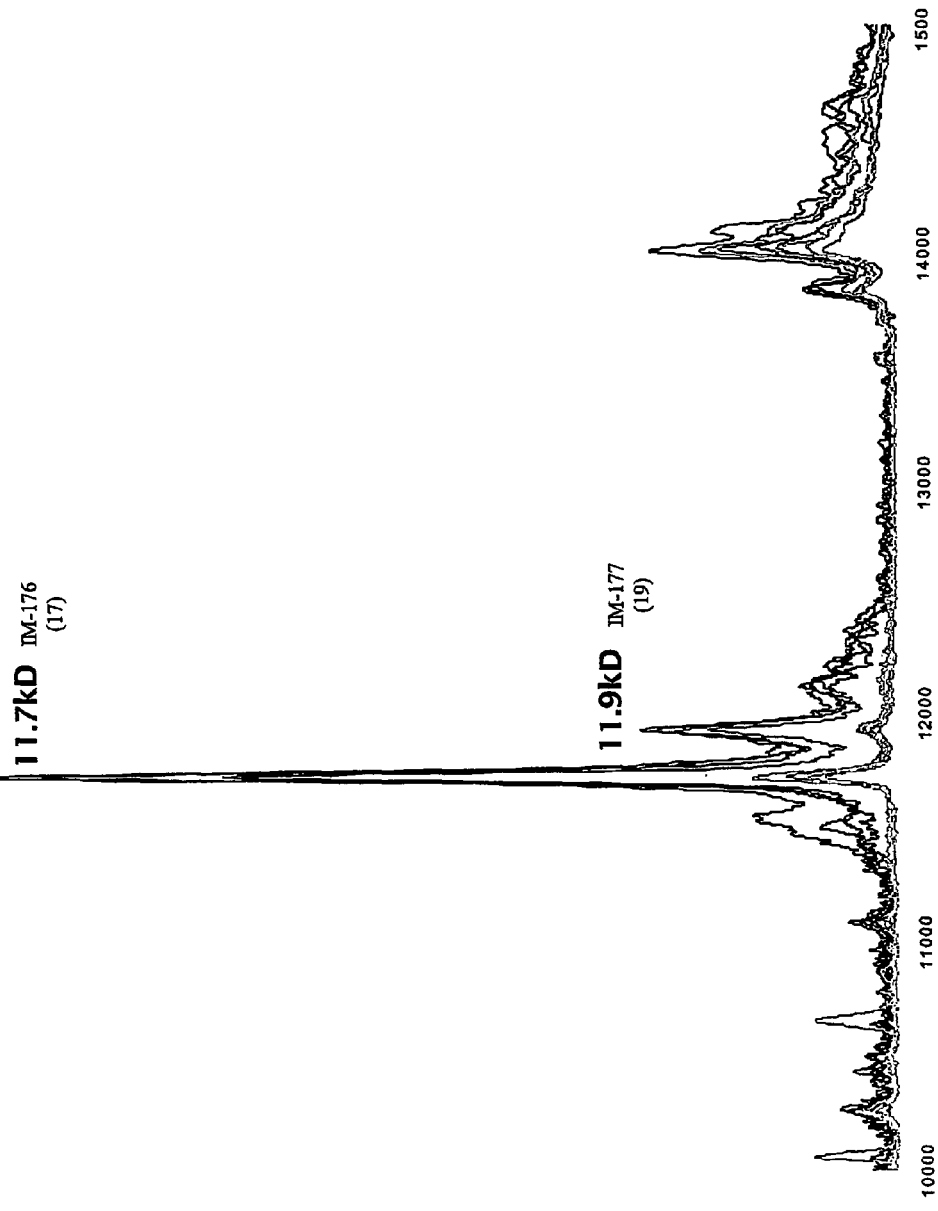
Figure 21:
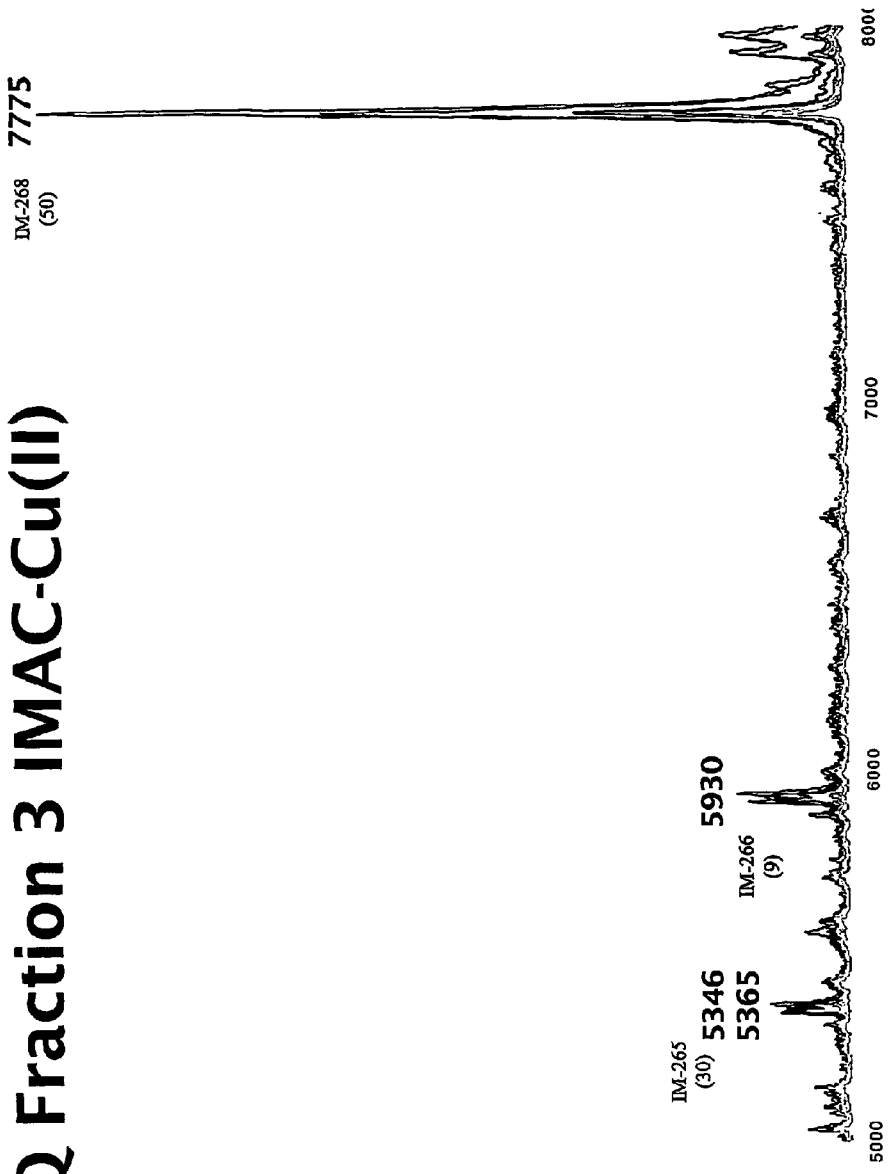
Figure 22:
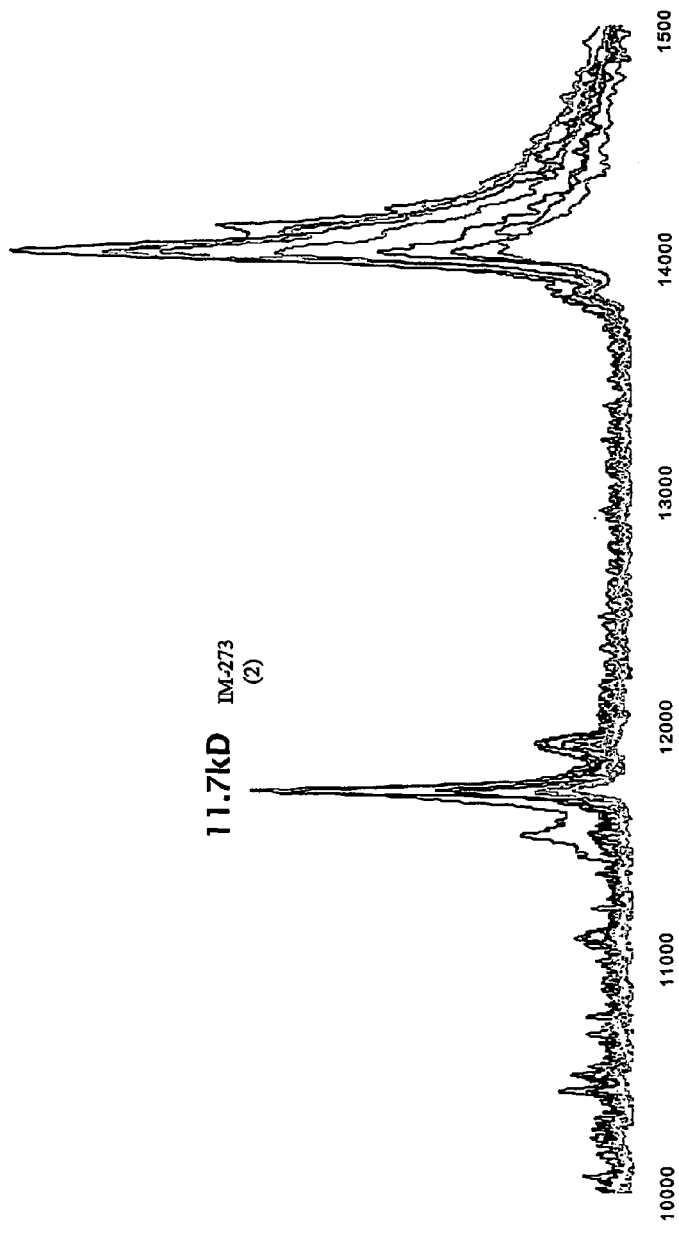
Figure 23:
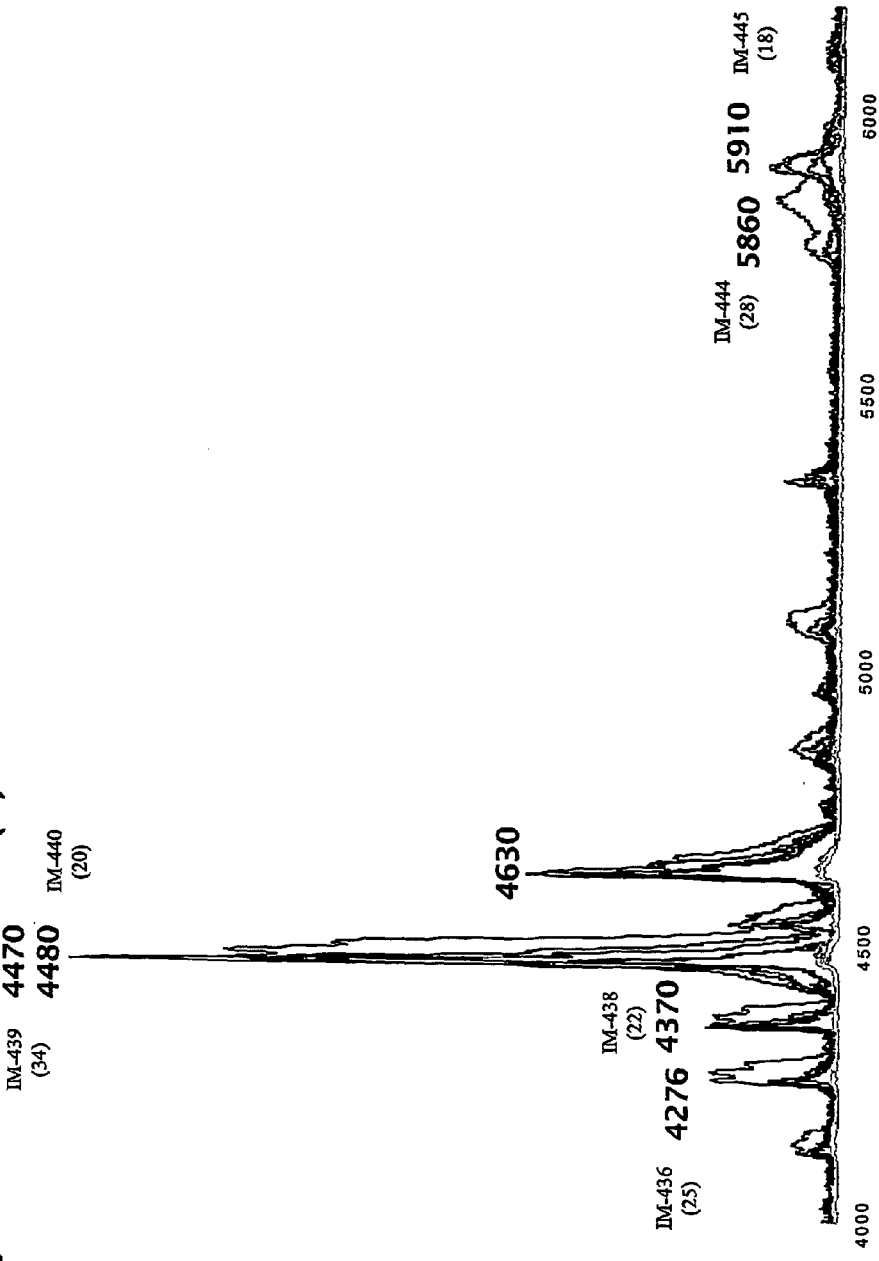
Figure 24:
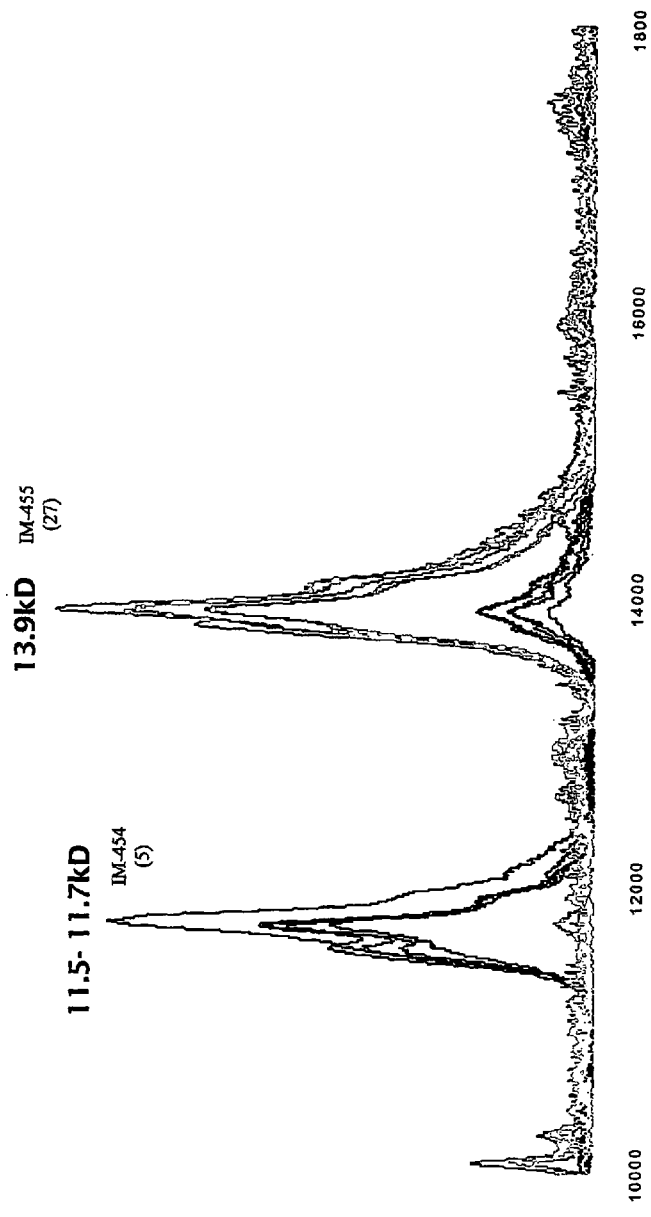
Figure 25:
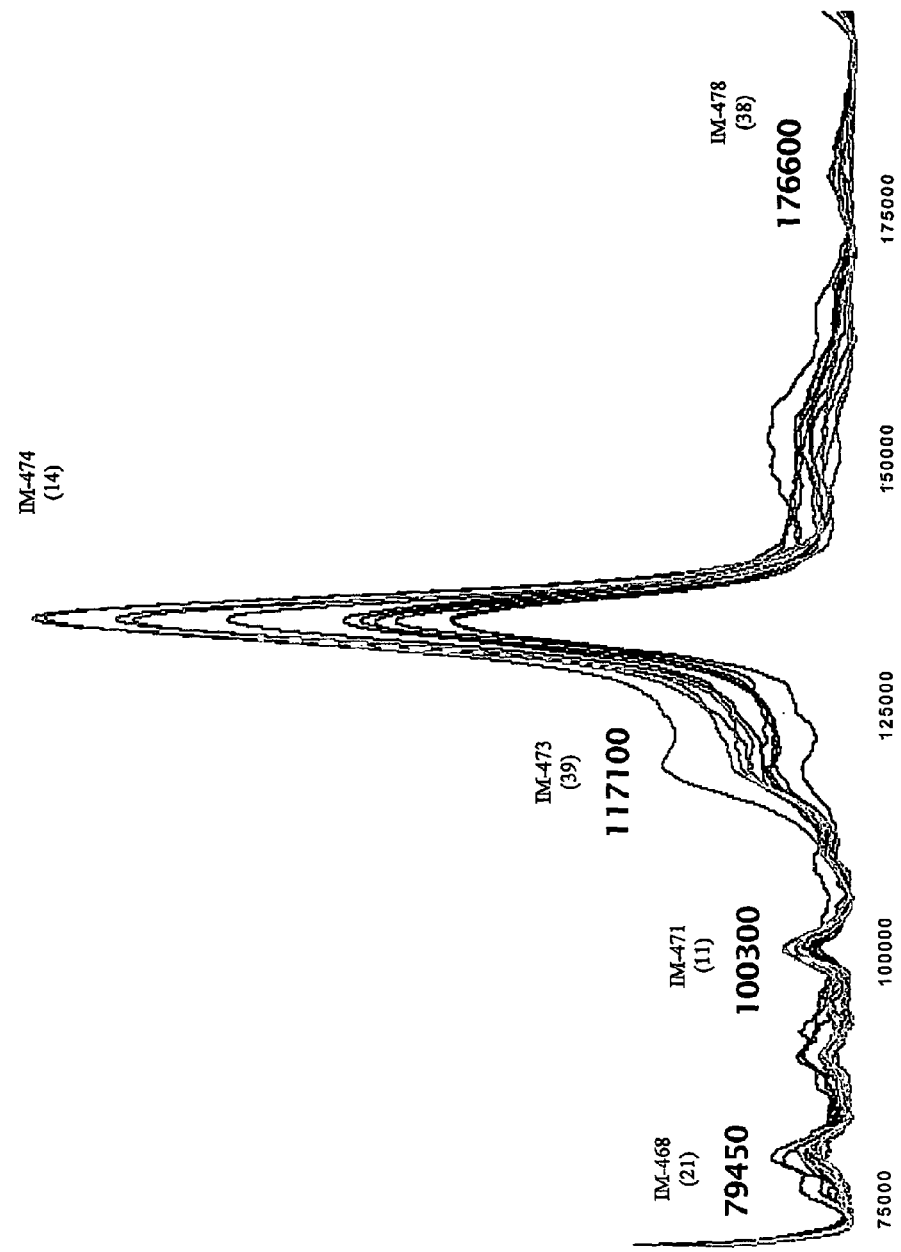
Figure 26:
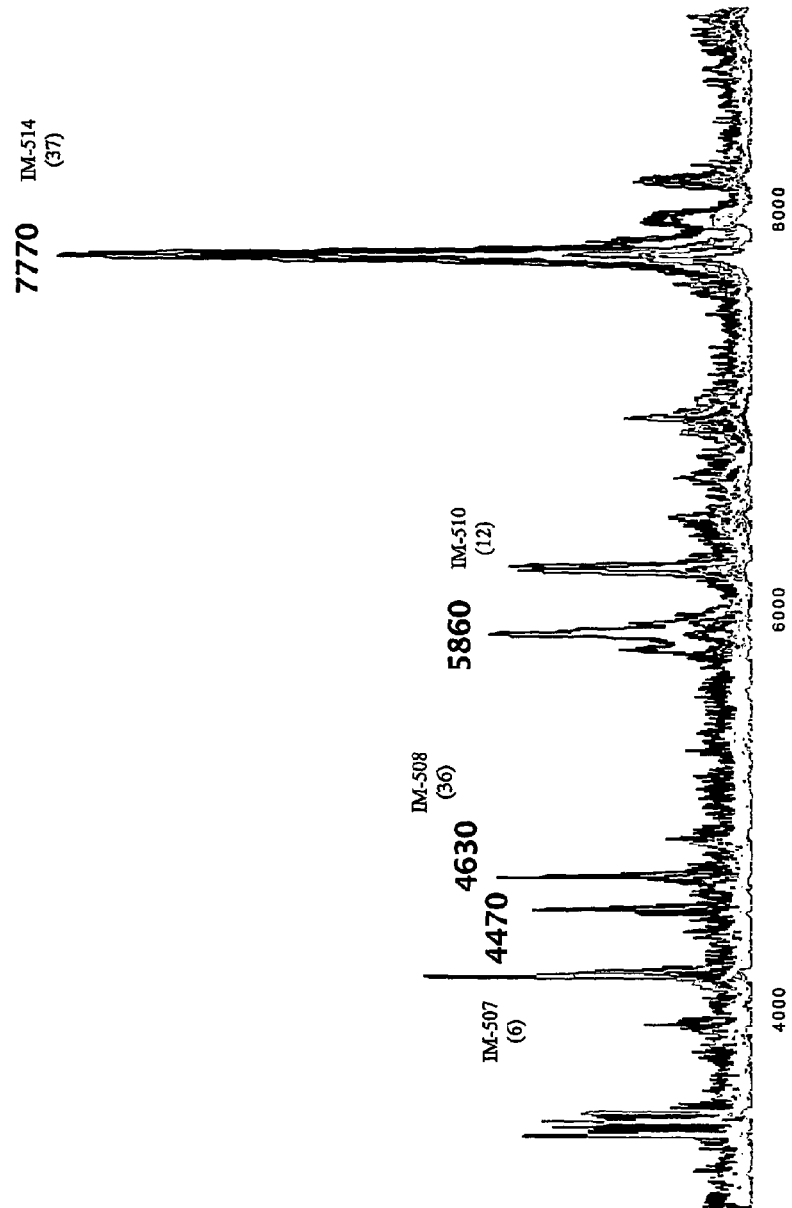
Figure 27:
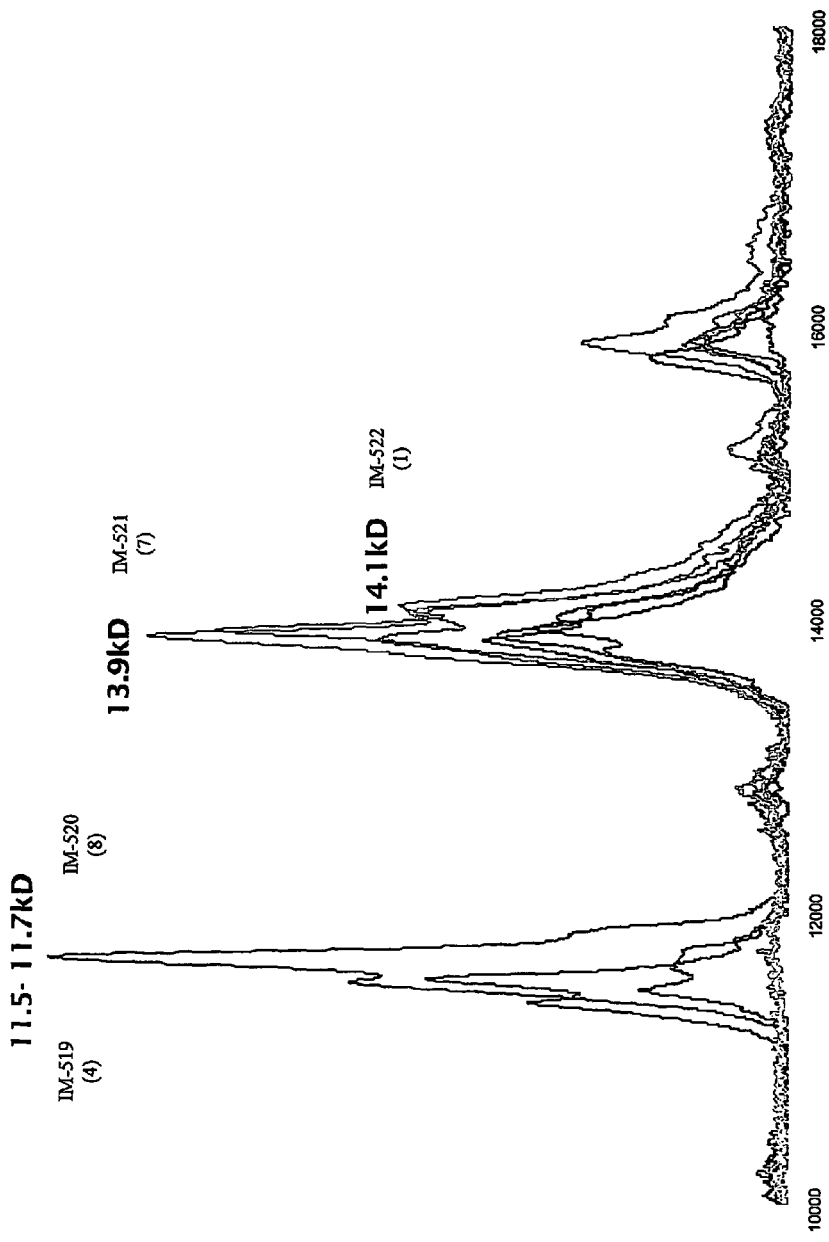

Several biomarkers identified in accordance with the teachings of the present invention fit to serum amyloid A (SAA) or to a fragment of SAA. SAA is a well-known acute phase inflammatory marker. A number of the SAA biomarkers are identified in FIG. 5 by both molecular mass and amino acid sequence. Most of these markers bound anti-SAA antibodies, as shown in FIG. 6. The intact mass of SAA is 11.5 to 11.7 kD, and these biomarkers also have been identified by the present methodology. Fragments preferably have a molecular mass of at least about 200 Daltons, more preferably at least about 500 Daltons. In even more preferred embodiments, fragments have a molecular mass of at least about 800 Daltons, and most preferably at least about 1 Kilodalton.

In one embodiment, the fragments of SAA include a sequence of amino acids that is recognized by an epitope of an anti-SAA antibody. One way of identifying suitable fragments for use in the present invention is to enzymatically digest SAA and test the resulting fragments for the ability to bind to an anti-SAA antibody. Fragments that bind anti-SAA antibody can be sequenced using techniques well-known in the art, although the sequence of the fragment is not needed to practice the invention. In order to practice the invention with a fragment from the enzymatic digest that is identified as binding anti-SAA antibody, all that is required is to subject to the fragment to mass spectrometry to determine its mass.

The serum biomarkers according to the present invention were identified by comparing mass spectra of samples derived from sera from two groups of newly-diagnosed subjects, subjects with lung cancer and normal subjects. The subjects were diagnosed according to standard clinical criteria. Lung cancer subjects were histologically confirmed, and subjects without lung cancer were followed for at least 18 months following serum collection for any sign of lung cancer, to exclude subjects with asymptomatic lung cancer.

Sera from each group of subjects was collected, and fractionated with Q Ceramic HyperDF ion exchange resin (Biosepra SA, France) into six fractions which eluted at different pH. Fraction A comprised the flow through plus pH 9 eluant, Fraction B comprised the pH 7 eluant, Fraction C comprised the pH 5 eluant, Fraction D comprised the pH 4 eluant, Fraction E comprised the pH 3 eluant, and Fraction F comprised isopropyl alcohol/acetonitrile TFA eluant. Fractions A through F are identified on FIGS. 7-28 as Fractions 1 through 6, respectively.

Each fraction was diluted and applied to a ProteinChip® array, either a Cu(II) IMAC3 or WCX2 chip array. Both of these chip arrays are produced by Ciphergen Biosystems, Inc. (Fremont, Calif.).

The Cu(II) IMAC3 is an "immobilized metal affinity-capture" chip, with a nitrilotriacetic acid surface for high-capacity copper binding and subsequent affinity capture of proteins with metal binding residues. Imidazole may be used in binding and washing solutions to moderate protein binding, including binding of non-specific proteins. Increasing the concentration of imidazole in the washing buffers reduces the binding of the target proteins. It is produced by photopolymerizing 5-methylacylamido-2-N,N-biscarboxymethylamino)pentanoic acid (7.5 wt %) and N,N'-methylenebisacrylamide (0.4 wt %) using (−) riboflavin (0.02 wt %) as a photoinitiator. The monomer solution is deposited onto the chip substrate and irradiated to photopolymerize. The chip then is activated with Cu(II).

The WCX2 is a weak cation exchange array with a carboxylate surface to bind cationic proteins. The negatively charged carboxylate groups on the surface of the WCX2 chip interact with the positive charges exposed on the target proteins. The binding of the target proteins is reduced by increasing the concentration of salt or by increasing the pH of the washing buffers.

Following application of the eluant fraction, the chips were incubated to allow the polypeptides in the eluant to bind to the sites on the chip by an affinity interaction. After incubation, each chip array was washed to remove polypeptides that bind non-specifically and buffer contaminants. That chip then was dried, and an energy absorbing molecule or matrix was applied to it, to facilitate desorption and ionization in a mass spectrometer.

In the mass spectrometer, retained polypeptides were desorbed from the chip array by laser desorption and ionization in a ProteinChip® Reader, which is integrated with ProteinChip® Software and a personal computer to analyze proteins captured on chip arrays. The ion optic and laser optic technologies in the ProteinChip® Reader detects proteins ranging from small peptides of less than 1000 Da up to proteins of 300 kilodaltons or more, and calculates the mass based on time-of-flight. Ionized polypeptides were detected and their mass accurately determined by this Time-of-Flight (TOF) Mass Spectrometry.

The mass spectra obtained for each group were subjected to scatter plot analysis, to eliminate run-to-run variation. Protein clusters on the scatter plot that had the same pattern for both lung cancer and normal subjects, i.e., protein clusters that were either elevated in both groups of subjects or depressed in both groups of subjects, were eliminated as potential biomarkers. The remaining polypeptides were further analyzed for their ability to accurately identify subjects with lung cancer. Because the molecular weights were derived from scatter plot analysis, and because of limits on the ability of mass spectrometry to resolve molecular weights, the "absolute" molecular weight values given in FIGS. 1A-1D and 3A-3O actually represent approximate molecular weights.

The biomarkers of this invention are characterized by their mass-to-charge ratio as determined by mass spectrometry. The mass-to-charge ratio of each biomarker is provided in FIGS. 1A-1D and 3A-3O. For example, IM-1 in FIG. 1A has a measured mass-to-charge ratio of 2011. The mass-to-charge ratios were determined from mass spectra generated on a Ciphergen Biosystems, Inc. PBS II mass spectrometer. This instrument has a mass accuracy of about +/−0.15 percent. Additionally, the instrument has a mass resolution of about 400 to 1000 m/dm, where m is mass and dm is the mass spectral peak width at 0.5 peak height. The mass-to-charge ratio of the biomarkers was determined using Biomarker Wizard™ software (Ciphergen Biosystems). Biomarker Wizard assigns a mass-to-charge ratio to a biomarker by clustering the mass-to-charge ratios of the same peaks from all the spectra analyzed, as determined by the PBSII, taking the maximum and minimum mass-to-charge-ratio in the cluster, and dividing by two. Accordingly, the masses provided reflect these specifications.

The biomarkers of this invention are further characterized by the shape of their spectral peak in time-of-flight mass spectrometry. Mass spectra showing peaks representing the biomarkers are presented in FIGS. 7-28. The biomarker identifier numbers from FIGS. 2 and 4A-4B, respectively, are shown next to the peak, along with their rank, which is indicated in parentheses below the biomarker identifier number.

The biomarkers of this invention are further characterized by their binding properties on chromatographic surfaces. Most of the biomarkers bind to IMAC (Cu) or WCX adsorbents (e.g., the Ciphergen® IMAC (Cu) or WCX ProteinChip® arrays) after washing as described herein.

Thus, a given molecular weight for a biomarker herein should be interpreted as the midpoint of a molecular-weight range. The accuracy of the mass spectrometer is +/−0.15%, and the actual molecular weight for a biomarker is therefore the value given, +/−0.15%. For example, the actual molecular weight for biomarker IM-273 is 11705+/−0.15%, or between 11687 and 11722. Often, the range surrounding the "absolute" value given in the figure is no more than +/−5 daltons (2006 to 2016 for IM-1), generally no more than +/−3 daltons (2008 to 2014 for IM-1), and often as small as +/−1 dalton (2010 to 2012 daltons for IM-1).

CART® (Salford Systems, San Diego, Calif.), a classification and regression tree software, was used to determine whether a potential biomarker had predictive value in assessing lung cancer. A software macro randomly selected a subset of 15% of the peaks from FIGS. 1A-1D or FIGS. 3A-3O. The peaks and peak heights from each sample were provided to the CARTS software for analysis. The software performed an iterative analysis until a single decision tree was generated that was capable of distinguishing between cancerous and non-cancerous. Each node in the resulting decision tree sorted based on the peak height of a single biomarker. A tree may contain any number of nodes, but generally contains from 1 to 6 nodes. From a practical standpoint in a commercial diagnostic test, a decision tree with fewer nodes is preferred. A total of 2000 decision trees, each based on a different 15% subset of the peaks from FIGS. 1A-1D or FIGS. 3A-3O, were generated.

The CART® software assigned a score to each biomarker in the subset, based on its relative importance. A score of 100 is very high and a score of 0 is very low. The CART® software also determined the sensitivity and specificity of each decision tree.

The data generated by the decision tree analysis was subjected to further analysis. The biomarkers were ranked based on their average scores, which were determined by adding up a biomarker's scores for each decision tree in which it appeared, and dividing by the total number of decision trees in which the biomarker appeared. Approximately 500 of the potential biomarkers showed up in at least one tree, and most of the biomarkers showed up in about 150 to 400 of the two thousand trees. The top 50 biomarkers for the IMAC and WCX chip arrays as determined by this method are shown in FIGS. 2 and 4A-4B, respectively.

All of the trees having sensitivities and specificities greater than 85% also were identified. All trees capable of distinguishing lung cancer from normal and having from 1 to 6 nodes that meet the 85/85 criterion are shown in Tables 1 and 2.

TABLE 1

Decision trees with IMAC Biomarkers.

2 Nodes

| | | | | |
|---|---|---|---|---|
| 474 | 151 | | | |
| 474 | 156 | | | |
| 522 | 507 | | 2 trees | |
| 522 | 440 | | 2 trees | |

3 Nodes

| | | |
|---|---|---|
| 266 | 454 | 474 |
| 474 | 156 | 153 |
| 474 | 40 | 156 |
| 520 | 276 | 113 |
| 520 | 265 | 401 |
| 522 | 151 | 474 |
| 522 | 478 | 153 |
| 522 | 156 | 474 |

4 Nodes

| | | | |
|---|---|---|---|
| 148 | 521 | 508 | 251 |
| 266 | 544 | 474 | 493 |
| 266 | 157 | 126 | 420 |
| 266 | 544 | 474 | 482 |
| 266 | 471 | 474 | 38 |
| 266 | 544 | 474 | 38 |
| 266 | 514 | 471 | 203 |
| 522 | 58 | 266 | 474 |

5 Nodes

| | | | | |
|---|---|---|---|---|
| 266 | 544 | 473 | 151 | 437 |
| 266 | 454 | 474 | 153 | 264 |
| 273 | 143 | 544 | 401 | 199 |

TABLE 2

Decision Trees with WCX Biomarkers.

1 Node

| |
|---|
| 446 |
| 447 |

2 Nodes

| | |
|---|---|
| 282 | 127 |

3 Nodes

| | | |
|---|---|---|
| 61 | 16 | 27 |
| 61 | 119 | 154 |
| 61 | 120 | 154 |
| 61 | 369 | 184 |
| 61 | 184 | 129 |
| 61 | 19 | 282 |
| 133 | 282 | 319 |
| 282 | 59 | 218 |
| 282 | 111 | 65 |
| 446 | 19 | 16 |

4 Nodes

| | | | |
|---|---|---|---|
| 61 | 369 | 282 | 184 |
| 61 | 48 | 203 | 3 |
| 446 | 369 | 111 | 67 |
| 446 | 466 | 58 | 120 |
| 446 | 19 | 59 | 113 |
| 446 | 282 | 19 | 47 |
| 447 | 118 | 59 | 417 |

TABLE 2-continued

Decision Trees with WCX Biomarkers.

| | | | | |
|---|---|---|---|---|
| 447 | 118 | 59 | 473 | |
| 447 | 65 | 59 | 275 | |
| 447 | 19 | 59 | 282 | |
| 447 | 369 | 59 | 206 | |
| 447 | 19 | 59 | 253 | |
| 447 | 19 | 47 | 70 | |

5 Nodes

| | | | | |
|---|---|---|---|---|
| 61 | 369 | 128 | 184 | 197 |
| 61 | 17 | 425 | 366 | 341 |
| 133 | 139 | 363 | 216 | 273 |
| 282 | 133 | 48 | 19 | 253 |
| 369 | 310 | 19 | 109 | 384 |
| 446 | 282 | 15 | 319 | 66 |
| 447 | 19 | 71 | 473 | 31 |
| 447 | 19 | 17 | 473 | 438 |
| 447 | 47 | 31 | 365 | 59 |

6 Nodes

| | | | | | |
|---|---|---|---|---|---|
| 369 | 366 | 192 | 471 | 19 | 439 |

Each of the biomarker combinations of Tables 1 and 2 are preferred combinations for distinguishing lung cancer subjects from normal subjects in accordance with the present invention.

All biomarkers that appeared in at least two of the trees that met the 85/85 criterion were identified. For these biomarkers, Tables 3 and 4 provide the number of times the biomarker occurred in a trees that met the criterion, as well as the ranking of that biomarker on the top 50 lists of FIGS. 2 and 4A-4B.

TABLE 3

Correlation of IMAC biomarker decision tree frequencies and ranking.

| Peak | # times | Rank |
|---|---|---|
| 266 | 9 | 9 |
| 522 | 8 | 1 |
| 474 | 4 | 14 |
| 520 | 2 | 3 |
| 148 | 1 | 8 |
| 273 | 1 | 2 |

TABLE 4

Correlation of WCX biomarker decision tree frequencies and ranking.

| Peak | # times | Rank |
|---|---|---|
| 447 | 11 | 2 |
| 61 | 10 | 1 |
| 446 | 7 | 3 |
| 282 | 4 | 9 |
| 369 | 2 | 8 |
| 133 | 2 | 4 |

Biomarkers that occurred frequently in the highly discriminatory trees occurred among the top 50 ranked biomarkers, and typically had a top 10 ranking. In addition, certain pairs of biomarkers reappear, e.g., WM-447 and WM-59, WM-447 and WM-19, WM-19 and WM-59, IM-266 and IM-474, IM-266 and IM-38, IM-266 and IM-454, IM-522 and IM-266. There also are repeats among triplets of biomarkers, such as IM-266, IM-266 and IM-38, and WM-447, WM-19 and WM-473. Other repeating pairs and trios of biomarkers can be seen in Tables 3 and 4, and are preferred.

Biomarkers and combinations of biomarkers identified in accordance with the present description may be used to qualify lung cancer status in a subject. In particular, a biomarker or combination of biomarkers can be used to distinguish lung cancer patients from normal patients with a high degree of specificity or sensitivity, i.e., greater than at least 85%, preferably greater than at least 90%, and more preferably greater than 95%.

According to one aspect of the invention, therefore, the detection of biomarkers for diagnosis of lung cancer status entails contacting a sample from a subject with a substrate, e.g., a SELDI probe, having an adsorbent thereon, under conditions that allow binding between the biomarker and the adsorbent, and then detecting the biomarker bound to the adsorbent by gas phase ion spectrometry, for example, mass spectrometry. Other detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

In one aspect, the markers of this invention are detect by gas phase ion spectrometry, which refers to the use of a gas phase ion spectrometer to detect gas phase ions. A gas phase ion spectrometer is an apparatus that detects gas phase ions. Gas phase ion spectrometers include an ion source that supplies gas phase ions. Gas phase ion spectrometers include, for example, mass spectrometers, ion mobility spectrometers, and total ion current measuring devices.

"Mass spectrometer" refers to a gas phase ion spectrometer that measures a parameter which can be translated into mass-to-charge ratios of gas phase ions. Mass Spectrometers generally include an ion source and a mass analyzer. Examples of mass spectrometers are time-of-flight, magnetic sector, quadrupole filter, ion trap, ion cyclotron resonance, electrostatic sector analyzer and hybrids of these. "Mass spectrometry" refers to the use of a mass spectrometer to detect gas phase ions. "Laser desorption mass spectrometer" refers to a mass spectrometer which uses laser as a means to desorb, volatilize, and ionize an analyte.

"Mass analyzer" refers to a sub-assembly of a mass spectrometer that comprises means for measuring a parameter which can be translated into mass-to-charge ratios of gas phase ions. In a time-of flight mass spectrometer the mass analyzer comprises an ion optic assembly, a flight tube and an ion detector.

"Ion source" refers to a sub-assembly of a gas phase ion spectrometer that provides gas phase ions. In one embodiment, the ion source provides ions through a desorption/ionization process. Such embodiments generally comprise a probe interface that positionally engages a probe in an interrogatable relationship to a source of ionizing energy (e.g., a laser desorption/ionization source) and in concurrent communication at atmospheric or subatmospheric pressure with a detector of a gas phase ion spectrometer.

Forms of ionizing energy for desorbing/ionizing an analyte from a solid phase include, for example: (1) laser energy; (2) fast atoms (used in fast atom bombardment); (3) high energy particles generated via beta decay of radionucleides (used in plasma desorption); and (4) primary ions generating secondary ions (used in secondary ion mass spectrometry). The preferred form of ionizing energy for solid phase analytes is a laser (used in laser desorption/ionization), in particular, nitrogen lasers, Nd-Yag lasers and other pulsed laser sources. "Fluence" refers to the laser energy delivered per unit area of interrogated image. Typically, a sample is placed on the surface of a probe, the probe is engaged with the probe interface and the probe surface is struck with the ionizing energy. The energy desorbs analyte molecules from the surface into the gas phase and ionizes them.

Other forms of ionizing energy for analytes include, for example: (1) electrons which ionize gas phase neutrals; (2) strong electric field to induce ionization from gas phase, solid phase, or liquid phase neutrals; and (3) a source that applies a combination of ionization particles or electric fields with neutral chemicals to induce chemical ionization of solid phase, gas phase, and liquid phase neutrals.

A preferred mass spectrometric technique for use in the invention is Surface Enhanced Laser Desorption and Ionization (SELDI), as described, for example, in U.S. Pat. Nos. 5,719,060 and 6,225,047, both to Hutchens and Yip, in which the surface of a probe that presents the analyte (here, one or more of the biomarkers) to the energy source plays an active role in desorption/ionization of analyte molecules. In this context, "probe" refers to a device adapted to engage a probe interface and to present an analyte to ionizing energy for ionization and introduction into a gas phase ion spectrometer, such as a mass spectrometer. A probe typically includes a solid substrate, either flexible or rigid, that has a sample-presenting surface, on which an analyte is presented to the source of ionizing energy.

One version of SELDI, called "Surface-Enhanced Affinity Capture" or "SEAC," involves the use of probes comprised of a chemically selective surface ("SELDI probe"). A "chemically selective surface" is one to which is bound either the adsorbent, also called a "binding moiety" or "capture reagent," or a reactive moiety that is capable of binding a capture reagent, e.g., through a reaction forming a covalent or coordinate covalent bond.

The phrase "reactive moiety" here denotes a chemical moiety that is capable of binding a capture reagent. Epoxide and carbodiimidizole are useful reactive moieties to covalently bind polypeptide capture reagents such as antibodies or cellular receptors. Nitriloacetic acid and iminodiacetic acid are useful reactive moieties that function as chelating agents to bind metal ions that interact non-covalently with histidine containing peptides. A "reactive surface" is a surface to which a reactive moiety is bound. An "adsorbent" or "capture reagent" can be any material capable of binding a biomarker of the invention. Suitable adsorbents for use in SELDI, according to the invention, are described in U.S. Pat. No. 6,225,047, supra.

One type of adsorbent is a "chromatographic adsorbent," which is a material typically used in chromatography. Chromatographic adsorbents include, for example, ion exchange materials, metal chelators, immobilized metal chelates, hydrophobic interaction adsorbents, hydrophilic interaction adsorbents, dyes, simple biomolecules (e.g., nucleotides, amino acids, simple sugars and fatty acids), mixed mode adsorbents (e.g., hydrophobic attraction/electrostatic repulsion adsorbents). "Biospecific adsorbent" is another category, for adsorbents that contain a biomolecule, e.g., a nucleotide, a nucleic acid molecule, an amino acid, a polypeptide, a polysaccharide, a lipid, a steroid or a conjugate of these (e.g. a glycoprotein, a lipoprotein, a glycolipid). In certain instances the biospecific adsorbent can be a macromolecular structure such as a multiprotein complex, a biological membrane or a virus. Illustrative biospecific adsorbents are antibodies, receptor proteins, and nucleic acids. A biospecific adsorbent typically has higher specificity for a target analyte than a chromatographic adsorbent.

Another version of SELDI is Surface-Enhanced Neat Desorption (SEND), which involves the use of probes comprising energy absorbing molecules that are chemically bound to the probe surface ("SEND probe"). The phrase "Energy absorbing molecules" (LAM) denotes molecules that are capable of absorbing energy from a laser desorption ionization source and, thereafter, contributing to desorption and ionization of analyte molecules in contact therewith. The EAM category includes molecules used in MALDI, frequently referred to as "matrix," and is exemplified by cinnamic acid derivatives, sinapinic acid (SPA), cyano-hydroxy-cinnamic acid (CHCA) and dihydroxybenzoic acid, ferulic acid, and hydroxyacetophenone derivatives. The category also includes EAMs used in SELDI, as enumerated, for example, by U.S. Pat. No. 5,719,060 and U.S. 60/351,971 (Kitagawa), filed Jan. 25, 2002.

Another version of SELDI, called Surface-Enhanced Photolabile Attachment and Release (SEPAR), involves the use of probes having moieties attached to the surface that can covalently bind an analyte, and then release the analyte through breaking a photolabile bond in the moiety after exposure to light, e.g., to laser light. For instance, see U.S. Pat. No. 5,719,060. SEPAR and other forms of SELDI are readily adapted to detecting a biomarker or biomarker profile, pursuant to the present invention.

The detection of the biomarkers according to the invention can be enhanced by using certain selectivity conditions, e.g., adsorbents or washing solutions. The phrase "wash solution" refers to an agent, typically a solution, which is used to affect or modify adsorption of an analyte to an adsorbent surface and/or to remove unbound materials from the surface. The elution characteristics of a wash solution can depend, for example, on pH, ionic strength, hydrophobicity, degree of chaotropism, detergent strength, and temperature.

Pursuant to one aspect of the present invention, a sample is analyzed by means of a "biochip," a term that denotes a solid substrate, having a generally planar surface, to which a capture reagent (adsorbent) is attached. Frequently, the surface of a biochip comprises a plurality of addressable locations, each of which has the capture reagent bound there. A biochip can be adapted to engage a probe interface and, hence, function as a probe in gas phase ion spectrometry preferably mass spectrometry. Alternatively, a biochip of the invention can be mounted onto another substrate to form a probe that can be inserted into the spectrometer.

A variety of biochips is available for the capture of biomarkers, in accordance with the present invention, from commercial sources such as Ciphergen Biosystems (Fremont, Calif.), Perkin Elmer (Packard BioScience Company (Meriden Conn.), Zyomyx (Hayward, Calif.), and Phylos (Lexington, Mass.). Exemplary of these biochips are those described in U.S. Pat. No. 6,225,047, supra, and No. 6,329,209 (Wagner et al.), and in PCT publications WO 99/51773 (Kuimelis and Wagner) and WO 00/56934 (Englert et al.).

More specifically, biochips produced by Ciphergen Biosystems have surfaces, presented on an aluminum substrate in strip form, to which are attached, at addressable locations, chromatographic or biospecific adsorbents. The surface of the strip is coated with silicon dioxide.

Illustrative of Ciphergen ProteinChip® arrays are biochips H4, SAX-2, WCX-2, and IMAC-3, which include a functionalized, cross-linked polymer in the form of a hydrogel, physically attached to the surface of the biochip or covalently attached through a silane to the surface of the biochip. The H4 biochip has isopropyl functionalities for hydrophobic binding. The SAX-2 biochip has quaternary ammonium functionalities for anion exchange. The WCX-2 biochip has carboxylate functionalities for cation exchange. The IMAC-3 biochip has nitriloacetic acid functionalities that adsorb transition metal ions, such as $Cu^{++}$ and $Ni^{++}$, by chelation. These immobilized metal ions, in turn, allow for adsorption of biomarkers by coordinate covalent bonding. Thus, Ciphergen's IMAC ProteinChip® arrays are sold with reactive moieties that become adsorbent upon the addition by the user of a metal solution.

In keeping with the above-described principles, a substrate with an adsorbent is contacted with the sample, containing serum, for a period of time sufficient to allow biomarker that may be present to bind to the adsorbent. In one embodiment of the invention, more than one type of substrate with adsorbent thereon is contacted with the biological sample. For example, a sample may be applied to both a WCX and an IMAC chip. This technique can allow for even more definitive assessment of cancer status. After the incubation period, the substrate is washed to remove unbound material. Any suitable washing solutions can be used; preferably, aqueous solutions are employed.

An energy absorbing molecule then is applied to the substrate with the bound biomarkers. As noted, an energy absorbing molecule is a molecule that absorbs energy from an energy source such as a laser, thereby assisting in desorption of biomarkers from the substrate. Exemplary energy absorbing molecules include, as noted above, cinnamic acid derivatives, sinapinic acid and dihydroxybenzoic acid. Preferably sinapinic acid is used.

The biomarkers bound to the substrates are detected in a gas phase ion spectrometer such as a time-of-flight mass spectrometer. The biomarkers are ionized by an ionization source such as a laser, the generated ions are collected by an ion optic assembly, and then a mass analyzer disperses and analyzes the passing ions. The detector then translates information of the detected ions into mass-to-charge ratios. Detection of a biomarker typically will involve detection of signal intensity. Thus, both the quantity and mass of the biomarker can be determined.

Data generated by desorption and detection of biomarkers can be analyzed with the use of a programmable digital computer. The computer program analyzes the data to indicate the number of markers detected, and optionally the strength of the signal and the determined molecular mass for each biomarker detected. Data analysis can include steps of determining signal strength of a biomarker and removing data deviating from a predetermined statistical distribution. For example, the observed peaks can be normalized, by calculating the height of each peak relative to some reference. The reference can be background noise generated by the instrument and chemicals such as the energy absorbing molecule which is set as zero in the scale.

The computer can transform the resulting data into various formats for display. The standard spectrum can be displayed, but in one useful format only the peak height and mass information are retained from the spectrum view, yielding a cleaner image and enabling biomarkers with nearly identical molecular weights to be more easily seen. In another useful format, two or more spectra are compared, conveniently highlighting unique biomarkers and biomarkers that are up- or down-regulated between samples. Using any of these formats, one can readily determine whether a particular biomarker is present in a sample.

Software used to analyze the data can include code that applies an algorithm to the analysis of the signal to determine whether the signal represents a peak in a signal that corresponds to a biomarker according to the present invention. The software also can subject the data regarding observed biomarker peaks to classification tree or ANN analysis, to determine whether a biomarker peak or combination of biomarker peaks is present that indicates lung cancer status. Analysis of the data may be "keyed" to a variety of parameters that are obtained either directly or indirectly from the mass spectrometric analysis of the sample. These parameters include, but are not limited to, the presence or absence of one or more peaks, the height of one or more peaks, the log of the height of one or more peaks, and other arithmetic manipulations of peak height data.

In another aspect, the present invention provides kits for aiding in the diagnosis of lung cancer status, which kits are used to detect biomarkers according to the invention. The kits screen for the presence of biomarkers and combinations of biomarkers that are differentially present in samples from normal subjects and subjects with lung cancer.

In one embodiment, the kit comprises a substrate having an adsorbent thereon, wherein the adsorbent is suitable for binding a biomarker according to the invention, and a washing solution or instructions for making a washing solution, in which the combination of the adsorbent and the washing solution allows detection of the biomarker using gas phase ion spectrometry, e.g., mass spectrometry. The kit may include more than type of adsorbent, each present on a different substrate.

In another embodiment, a kit of the invention may include a first substrate, comprising an adsorbent thereon, and a second substrate onto which the first substrate is positioned to form a probe, which can be inserted into a gas phase ion spectrometer, e.g., a mass spectrometer. In another embodiment, an inventive kit may comprise a single substrate that can be inserted into the spectrometer.

In a further embodiment, such a kit can comprise instructions for suitable operational parameters in the form of a label or separate insert. For example, the instructions may inform a consumer how to collect the sample or how to wash the probe. In yet another embodiment the kit can comprise one or more containers with biomarker samples, to be used as standard(s) for calibration.

In a preferred embodiment, the detection of biomarkers for diagnosis of lung cancer in a subject entails contacting a sample from a subject or patient, preferably a serum sample, with a substrate having an adsorbent thereon under conditions that allow binding between the biomarker and the adsorbent, and then detecting the biomarker bound to the adsorbent by gas phase ion spectrometry, preferably by Surface Enhanced Laser Desorption/Ionization (SELDI) mass spectrometry. The biomarkers are ionized by an ionization source such as a laser. The generated ions are collected by an ion optic assembly and accelerated toward an ion detector. Ions that strike the detector generate an electric potential that is digitized by a high speed time-array recording device that digitally captures the analog signal. Ciphergen's ProteinChip® system employs an analog-to-digital converter (ADC) to accomplish this. The ADC integrates detector output at regularly spaced time intervals into time-dependent bins. The time intervals typically are one to four nanoseconds long. Furthermore, the time-of-flight spectrum ultimately analyzed typically does not represent the signal from a single pulse of ionizing energy against a sample, but rather the sum of signals from a number of pulses. This reduces noise and increases dynamic range. This time-of-flight data is then subject to data processing. In Ciphergen's ProteinChip® software, data processing typically includes TOF-to-M/Z transformation, baseline subtraction, high frequency noise filtering. Thus, both the quantity and mass of the biomarker can be determined.

The detection of the biomarkers can be enhanced by using certain selectivity conditions, e.g., adsorbents or washing solutions. In one embodiment, the same or similar selectivity conditions that were used to discover the biomarkers are used in the method of detecting the biomarker in the sample. For example, immobilized metal affinity capture chips such as the Cu(II) IMAC3 and weak cationic exchange chips such as the WCX2 chips are preferred as the adsorbents for biomarker detection. However, other adsorbents can be used, as long as they have the binding characteristics suitable for binding the biomarkers.

More particularly, armed with the information regarding the biomarkers identified herein, various methods can be used to recognize patterns of doublets, triplets, and higher combinations of biomarkers according to the invention. These methods take raw data regarding which peaks are present and their intensity and provide a differential diagnosis of lung cancer versus normal for a sample.

Thus, the process can be divided into the learning phase and the classification phase. In the learning phase, a learning algorithm is applied to a data set that includes members of the different classes that are meant to be classified, for example, data from a plurality of samples diagnosed as cancer and data from a plurality of samples assigned a negative diagnosis. The methods used to analyze the data include, but are not limited to, artificial neural network, support vector machines, genetic algorithm and self-organizing maps and classification and regression tree analysis. These methods are described, for example, in WO 01/31579, May 3, 2001 (Barnhill et al.); WO 02/06829, Jan. 24, 2002 (Hitt et al.) and WO 02/42733, May 30, 2002 (Paulse et al.). The learning algorithm produces a classifying algorithm. The classifier is keyed to elements of the data, such as particular markers and particular intensities of markers, usally in combination, that can classify an unknown sample into one of the two classes. The classifier is ultimately used for diagnostic testing.

Software, both freeware and proprietary software, is readily available to analyze such patterns in data, and to devise additional patterns with any predetermined criteria for success. Those biomarkers which by themselves are predictive of a differential diagnosis of lung cancer versus normal do not require pattern recognition software to analyze the data.

The following examples are offered by way of illustration, and are not limiting.

EXAMPLE I

Fractionation of Serum

Buffers:
1. U9 (9M urea, 2% CHAPS, 50 mM Tris-HCl pH9)
2. U1 (1M urea, 0.22% CHAPS, 50 mM Tris-HCl pH9)
3. wash buffer 1: 50 mM Tris-HCl with 0.1% n-octyl α-D-Glucopyranoside (OGP) pH9
4. wash buffer 2: 100 mM sodium phosphate with 0.1% OGP pH7
5. wash buffer 3: 100 mM sodium acetate with 0.1% OGP pH5
6. wash buffer 4: 100 mM sodium acetate with 0.1% OGP pH4
7. wash buffer 5: 50 mM sodium citrate with 0.1% OGP pH3
8. wash buffer 6: 33.3% isopropanol/16.7% acetonitrile/0.1% trifluoroacetic acid in water.

Thirty microliters of U9 buffer were added to 20 μL of serum in a tube and were mixed at 4° C. for 20 minutes. Ion exchange resin (Q Ceramic HyperDF ion exchange resin, Biosepra SA, France) was washed 3 times with 5 bed volumes of 50 mM Tris-HCl pH9 and stored in 50% suspension. To each well of a 96-well filter plate (96-well Silent Screen filter plate, Loprodyne membrane, 0.45 micron pore, Nalge Nunc International, USA), 125 µL of ion exchange resin (50% suspension) was added on a Biomek 2000 Automation Workstation (Beckman Coulter, Fullerton, Calif.), washed 3 times with 150 µL U1 buffer, and vacuum dried. Urea-treated serum was transferred to each well of ion exchange resin. The serum tube was rinsed with 50 µL of U1 buffer, which was also transferred to the corresponding well in filter plate. The filter plate was mixed on a platform shaker at 4° C. for 30 minutes. Flow-through fraction was collected in a 96-well plate by vacuum suction (Fraction 1). Then, 100 µL of wash buffer 1 was added to each well of filter plate and mixed for 10 minutes at room temperature. Eluant was collected into the same 96-well plate (Fraction 1). Resins in the filter plate were subsequently washed two times each with 100 µL wash buffers 2, 3, 4, 5 and 6. Each eluant (total volume of 200 µL) was collected in a 96-well plate (fractions 2, 3, 4, 5 and 6).

EXAMPLE 2

SELDI Analysis of Fractionated Serum

ProteinChip® Arrays were set up in 96-well bioprocessors. Buffer delivery and sample incubation were performed on a Biomek 2000 Automation Workstation. Each serum fraction was analyzed on IMAC3 (loaded with copper) and WCX2 ProteinChip® Arrays in duplicates. IMAC3 copper and WCX2 arrays (Ciphergen Biosystems Inc, Fremont, Calif.) were equilibrated two times with 150 µL of binding buffer (100 mM sodium phosphate+0.5M NaCl pH7 for IMAC3, 100 mM sodium acetate pH4 for WCX2). Each serum fraction was diluted in the corresponding binding buffer (1/5 dilution for IMAC3 and 1/10 dilution for WCX2) and 100 µL was applied to each ProteinChip® array. Incubation was performed on a platform shaker at room temperature for 30 minutes. Each array was washed three times with 150 µL of corresponding binding buffer and rinsed two times with water. ProteinChip® arrays were air-dried. Sinapinic acid matrix (prepared in 50% acetonitrile, 0.5% trifluoroacetic acid) was applied to each array. ProteinChip® arrays were read on a ProteinChip® PBSII Reader (Ciphergen Biosystems Inc.) A total of 253 laser shots were averaged for each array.

All publications and patent documents cited in this application are incorporated by reference in their entirety for all purposes to the same extent as if each individual publication or patent document were so individually denoted. By their citation of various references in this document Applicants do not admit that any particular reference is "prior art" to their invention.

What we claim is:

1. A tangible computer-readable medium having computer-executable instructions for performing a method of qualifying lung carcinoma status in a subject, which method comprises: (A) transforming data extracted from a spectrum generated by mass spectroscopic analysis of a biological sample taken from the subject to identify component peaks of the spectrum; and then (B) matching the peaks to biomarker sets listed in Table 1 or Table 2, wherein positive matches to the biomarker sets are useable to qualify lung cancer.

2. A tangible computer-readable medium according to claim 1, wherein the data extracted is characterized by binding to IMAC or WCX adsorbents.

3. A tangible computer-readable medium according to claim 1, wherein said method further comprises qualifying lung cancer in the subject.

* * * * *